(12) United States Patent
Tanaka et al.

(10) Patent No.: US 11,401,296 B2
(45) Date of Patent: Aug. 2, 2022

(54) AMIDITE COMPOUND AND METHOD FOR PRODUCING POLYNUCLEOTIDE USING SAID COMPOUND

(71) Applicant: SUMITOMO CHEMICAL COMPANY, LIMITED, Chuo-ku (JP)

(72) Inventors: Yuki Tanaka, Osaka (JP); Tatsuya Saito, Osaka (JP); Hideki Ihara, Osaka (JP)

(73) Assignee: SUMITOMO CHEMICAL COMPANY, LIMITED, Chuo-ku (JP)

(*) Notice: Subject to any disclaimer, the term of this patent is extended or adjusted under 35 U.S.C. 154(b) by 113 days.

(21) Appl. No.: 17/049,905

(22) PCT Filed: Apr. 23, 2019

(86) PCT No.: PCT/JP2019/017249
§ 371 (c)(1),
(2) Date: Oct. 22, 2020

(87) PCT Pub. No.: WO2019/208571
PCT Pub. Date: Oct. 31, 2019

(65) Prior Publication Data
US 2021/0238217 A1  Aug. 5, 2021

(30) Foreign Application Priority Data

Apr. 24, 2018 (JP) .............................. JP2018-083148
Jul. 27, 2018 (JP) .............................. JP2018-141559

(51) Int. Cl.
C07H 23/00 (2006.01)
C07C 253/16 (2006.01)
C07H 21/02 (2006.01)

(52) U.S. Cl.
CPC ........... *C07H 23/00* (2013.01); *C07C 253/16* (2013.01); *C07H 21/02* (2013.01)

(58) Field of Classification Search
CPC ........ C07H 21/00; C07H 21/02; C07C 253/16
See application file for complete search history.

(56) References Cited

U.S. PATENT DOCUMENTS

| 2007/0282097 A1 | 12/2007 | Ohgi et al. |
| 2011/0178284 A1 | 7/2011 | Wada et al. |
| 2012/0035246 A1 | 2/2012 | Ohgi et al. |
| 2013/0253178 A1 | 9/2013 | Shimizu et al. |
| 2014/0206856 A1 | 7/2014 | Aoki et al. |

FOREIGN PATENT DOCUMENTS

| EP | 1795536 A1 | 6/2007 |
| EP | 2749565 A1 | 7/2014 |
| JP | 2008-174524 A | 7/2008 |
| JP | 5157168 B2 | 3/2013 |
| JP | 5554881 B2 | 7/2014 |
| JP | 2016050203 A | 4/2016 |
| WO | WO 2008/090829 A1 | 7/2008 |
| WO | WO 2011/034072 A1 | 3/2011 |

(Continued)

OTHER PUBLICATIONS

International Search Report dated Jul. 9, 2019 in PCT/JP2019/017249 (submitting English translation only), 2 pages.
International Preliminary Report on Patentability and Written Opinion of the International Searching Authority dated Oct. 27, 2020 in PCT/JP2019/017249 filed Apr. 23, 2019 (submitting English translation only), 4 pages.
Extended European Search Report dated Dec. 10, 2021 in European Patent Application No. 19792159.6, 13 pages.
Tadaaki Ohgi, et al., "A New RNA Synthetic Method with a 2'-0-(2-Cyanoethoxymethyl) Protecting Group" Organic Letters, American Chemical Society, US, XP003009345, vol. 7, No. 16, Jan. 1, 2005, pp. 3477-3480.

(Continued)

*Primary Examiner* — Jonathan S Lau
(74) *Attorney, Agent, or Firm* — Oblon, McClelland, Maier & Neustadt, L.L.P.

(57) ABSTRACT

The present invention provides an amidite compound represented by formula (1) which enables a synthesis of RNA with high purity, and the method for preparing a polynucleotide by using the same compound. (In the formula (1), wherein R represents the following formula (wherein $R^a$ and $R^b$ are identical to or different from each other and each represents a methyl group, an ethyl group, or a hydrogen atom, with the proviso that $R^a$ and $R^b$ does not represent a hydrogen atom, n is an integer of 1 to 5), and $B^a$ represents a group containing optionally protected nucleobase structure, and $G^1$ and $G^2$ are identical to or different from each other and each represents a protecting group for a hydroxy group, and $G^3$ are identical to or different from each other and each represents an alkyl group.

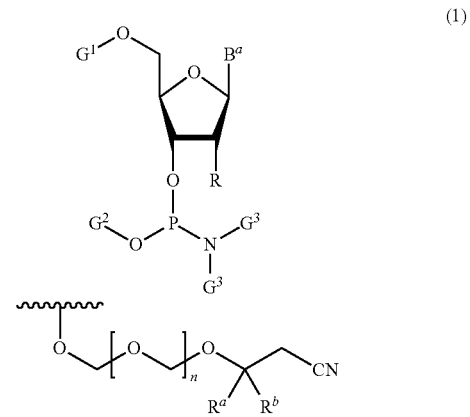

23 Claims, No Drawings
Specification includes a Sequence Listing.

(56) References Cited

FOREIGN PATENT DOCUMENTS

| WO | WO 2012/073857 A1 | 6/2012 |
| WO | WO 2013/027843 A1 | 2/2013 |
| WO | WO 2017/188042 A1 | 11/2017 |

OTHER PUBLICATIONS

Indian Office Action dated Dec. 22, 2021 in Indian Patent Application No. 202017046101, 6 pages.

SEQUENCE LISTING

```
<160> NUMBER OF SEQ ID NOS: 3

<210> SEQ ID NO 1
<211> LENGTH: 50
<212> TYPE: RNA
<213> ORGANISM: Artificial Sequence
<220> FEATURE:
<223> OTHER INFORMATION: uridine 50-mer

<400> SEQUENCE: 1
uuuuuuuuuu uuuuuuuuuu uuuuuuuuuu uuuuuuuuuu uuuuuuuuuu          50

<210> SEQ ID NO 2
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 2
agcagaguac acacagcaua uacc                                      24

<210> SEQ ID NO 3
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 3
gguauaugcu guguguacuc ugcuuc                                    26
```

AMIDITE COMPOUND AND METHOD FOR PRODUCING POLYNUCLEOTIDE USING SAID COMPOUND

TECHNICAL FIELD

This application claims priority to and the benefit of Japanese Patent Application No. 2018-083148 filed Apr. 24, 2018 and Japanese Patent Application No. 2018-141559 filed Jul. 27, 2018, the entire contents of which are incorporated herein by reference.

The present invention relates to an amidite compound and a process for preparing polynucleotide using the same compound. Further the present invention relates to an intermediate compound for the amidite compound and the process for preparing the same intermediate compound.

BACKGROUND ART

RNA can be applied as RNA probe, antisense RNA, ribozyme, siRNA, and aptamer, which is a useful material.

RNA can be synthesized according to solid phase synthesis method and so on, and in the solid phase synthesis, phosphoramidite of nucleotide (hereinafter, referred to as "amidite") is used as a raw material. As examples of the protecting group of a hydroxy group at 2' position of the amidite, TBDMS (t-butyl dimethyl silyl), TOM (triisopropyl silyloxy methyl), ACE (bis(2-acetoxyethoxy)methyl) and the others. Further, though the protecting groups which are disclosed in the patent documents 1 and 2 have been reported, it is not necessarily sufficient for the synthesis method of RNA by using an amidite containing these protecting groups in terms of a yield or a purity of the obtained RNA.

CITATION LIST

Patent Document

Patent Document 1: JP Patent No. 5157168 B2
Patent Document 2: JP Patent No. 5554881 B2

SUMMARY OF THE INVENTION

Problems to be Solved by Invention

An object of the present invention is to provide an amidite compound that enables a synthesis of RNA with high purity, and a method for preparing polynucleotide by using the same compound. Further an object of the present invention is to provide an intermediate compound fox the amidite compound, and the method for preparing the same intermediate compound.

Means to Solve Problems

The present inventors have intensively studied to achieve the objects, and as a result, found that use of the following group as a protecting group for a hydroxy group at 2' position of the amidite can lead to production of RNA with high purity.

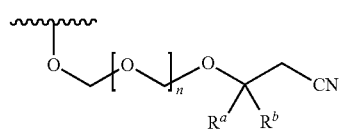

wherein $R^a$ and $R^b$ are identical to or different from each other and each represents a methyl group, an ethyl group, or a hydrogen atom, with the proviso that $R^a$ and $R^b$ do not represent a hydrogen atom at the same time, and n is an integer of 1 to 5.

The present invention has been completed after further examinations on the basis of these findings, and as a result, provides the following amidite compound, a method for preparing polynucleotide using the same compound, an ether compound, and a method for preparing the ether compound.

The present invention includes the following embodiments, but is not limited thereto.

Item 1. An amidite compound represented by formula (1):

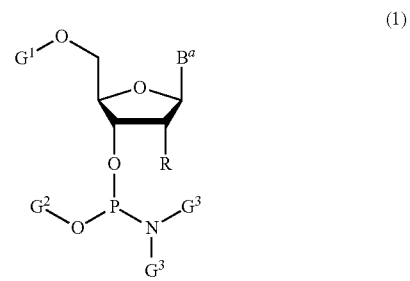

wherein

R represents a formula:

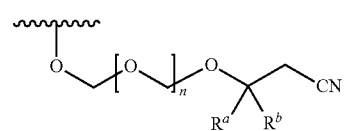

wherein $R^a$ and $R^b$ are identical to or different from each other and each represents a methyl group, an ethyl group, or a hydrogen atom, with the proviso that $R^a$ and $R^b$ do not represent a hydrogen atom at the same time, n represents an integer of 1 to 5, $B^a$ represents a group containing optionally-protected nucleobase structure, $G^1$ and $G^2$ are identical to or different from each other and each represents a protecting group for a hydroxy group, and $G^3$ are identical to or different from each other and each represents an alkyl group.

Item 2. The amidite compound according to Item 1 wherein $R^a$ represents a methyl group or an ethyl group, and $R^b$ represents a hydrogen atom.

Item 3. The amidite compound according to Item 1 or 2 wherein G¹ represents the below-mentioned group:

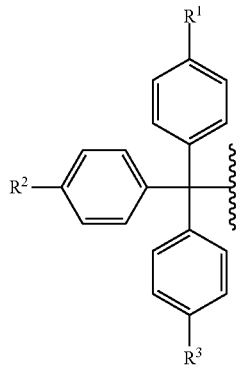

wherein

R¹, R² and R³ are identical to or different from each other, and each represents a hydrogen atom or an alkoxy group.

Item 4. The amidite compound according to any one of Items 1 to 3 wherein G² represents the following group:

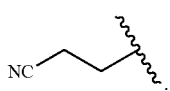 [SMILES: *CCC#N]

Item 5. The amidite compound according to any one of Items 1 to 4 wherein G³ represents an isopropyl group.

Item 6. A method for preparing a compound containing a polynucleotide structure represented by formula (2):

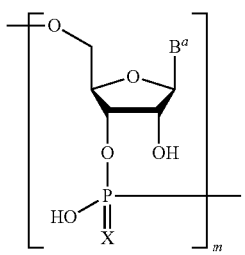

(2)

wherein $B^a$ is identical to or different from each other and each represents a group containing optionally-protected nucleobase structure, X represents an oxygen atom or a sulfur atom, and m is a positive integer, which comprises a step of subjecting the amidite compound according to any one of Items 1 to 5 to a solid phase reaction.

Item 7. The method according to Item 6 wherein the compound containing the polynucleotide structure represented by formula (2) is a compound resulting from the step of reacting a compound represented by formula (3):

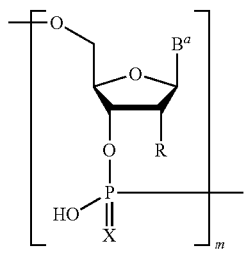

(3)

wherein $B^a$ is identical to or different from each other and each represents a group containing optionally-protected nucleobase structure, X represents an oxygen atom or a sulfur atom, R is identical to or different from each other and each represents a formula:

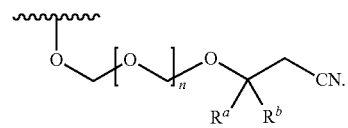

wherein $R^a$ and $R^b$ are identical to or different from each other and each represents a methyl group, an ethyl group, or a hydrogen atom, with the proviso that $R^a$ and $R^b$ do not represent a hydrogen atom at the same time, n represents an integer of 1 to 5, m is a positive integer, with tetraalkylammonium fluoride in a solid phase synthesis reaction utilizing the amidite compound.

Item 8. The method according to Item 7 wherein $R^a$ represents a methyl group or an ethyl group, and $R^b$ represents a hydrogen atom.

Item 9. The method according to any one of claims 6 to 8 wherein n=1.

Item 10. An ether compound represented by formula (4).

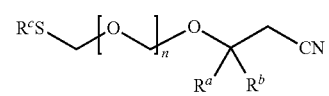

(4)

wherein $R^a$, $R^b$ and n are the same as defined in Item 1, and $R^c$ represents a C1-C6 alkyl group or a phenyl group.

Item 11. The ether compound according to Item 10 wherein $R^a$ represents a methyl group or an ethyl group, $R^b$ represents a hydrogen atom, and $R^c$ represents a methyl group.

Item 12. The compound according to Item 10 or 11 wherein n=1.

Item 13. A method for preparing an ether compound represented by formula (7):

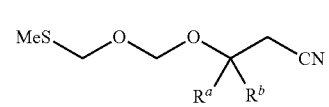

(7)

wherein $R^a$ and $R^b$ are the same as defined below, which comprises the steps of:

(a): reacting a compound represented by formula (5):

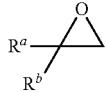
(5)

wherein $R^a$ and $R^b$ are identical to or different from each other and each represents a methyl group, an ethyl group, or a hydrogen atom, with the proviso that $R^a$ and $R^b$ do not represent a hydrogen atom at the same time, with a cyanide ion, and (b): reacting 3-hydroxyalkylnitrile represented by formula (6):

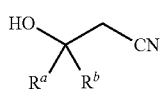
(6)

wherein $R^a$ and $R^b$ are the same as defined above, which is obtained by the step (a), with bis(methylthiomethyl)ether in a solvent in the presence of an oxidizing agent and an acid.

Item 14. The method according to Item 13 wherein $R^a$ represents a methyl group or an ethyl group, and $R^b$ represents a hydrogen atom.

Item 15. The method according to Item 13 wherein $R^a$ represents a methyl group, and $R^b$ represents a hydrogen atom.

Item 16. The method according to Item 15 for preparing a compound represented by formula (8):

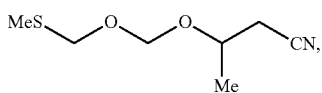
(8)

which comprises the steps of:

A: hydrolyzing 3-aminocrotononitrile,

B: reducing the cyanoacetone obtained by the step A to obtain 3-hydroxybutanenitrile, and C: reacting the 3-hydroxybutanenitrile obtained by the step B with bis(methylthiomethyl)ether in a solvent in the presence of an oxidizing agent and an acid.

Item 17. A method for preparing a compound represented by formula (10):

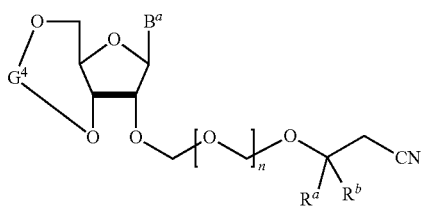
(10)

wherein $B^a$, $R^a$, $R^b$, n and $G^4$ are the same as defined below, which comprises reacting a compound represented by formula (9):

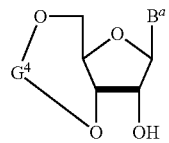
(9)

wherein $B^a$ represented a compound containing optionally-protected nucleobase structure, and $G^4$ represents a protecting group for a hydroxy group, with a compound represented by formula (4):

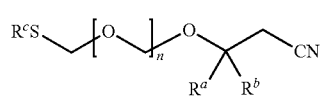
(4)

wherein $R^a$ and $R^b$ are identical to or different from each other and each represents a methyl group, an ethyl group, or a hydrogen atom, with the proviso that $R^a$ and $R^b$ do not represent a hydrogen atom at the same time, $R^c$ represents a C1-C6 alkyl group or a phenyl group, and n is an integer of 1 to 4.

in the presence of an oxidizing agent.

Item 18. The method according to Item 17 wherein tetrahydropyran or 4-methyltetrahydropyran is used as a reaction solvent.

Item 19. A method for preparing the compound represented by formula (1) as defined in claim 1, which comprises further steps of:

deprotecting the compound represented by formula (10) to obtain the compound represented by formula (11):

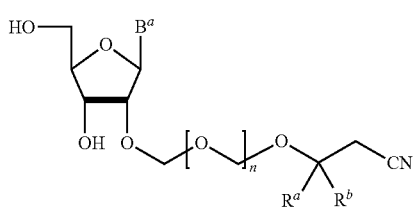
(11)

wherein $B^a$, $R^a$, $R^b$ and n are the same as defined above, protecting selectively a hydroxy group at 5' position of the compound represented by formula (11) to obtain a compound represented by formula (12):

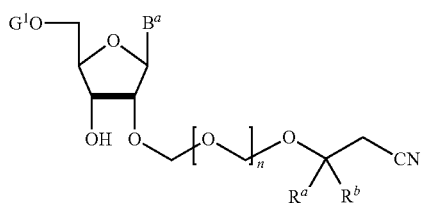

(12)

wherein

B$^a$, R$^a$, R$^b$ and n are the same as defined above, and G$^1$ represents a protecting group for a hydroxy group, and reacting the compound represented by formula (12) with a phosphorodiamidite represented by formula (13):

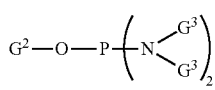

(13)

wherein

G$^2$ represents a protecting group for a hydroxy group, and G$^3$ are identical to or different from each other and each represents an alkyl group.

Item 20. The method according to Item 19 wherein G$^4$ represents a group represented by a G$^4$-1 or G$^4$-2 structure.

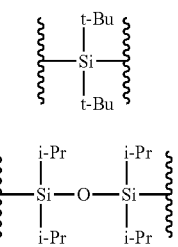

Item 21. A compound represented by formula (10):

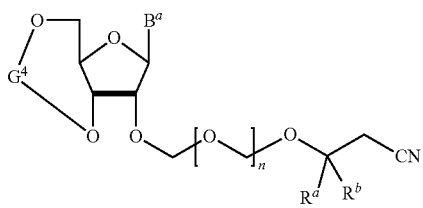

(10)

wherein

R$^a$ and R$^b$ are identical to or different from each other, and each represents a methyl group, an ethyl group, or a hydrogen atom, with the proviso that R$^a$ and R$^b$ do not represent a hydrogen atom at the same time, n is an integer of 1 to 5, B$^a$ represents a group containing an optionally protected nucleobase structure, and G$^4$ represents a protecting group.

Item 22. A compound represented by formula (11):

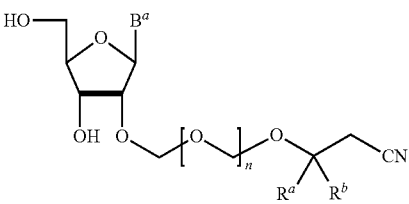

(11)

wherein

B$^a$, R$^a$, R$^b$ and n are the same as defined in Item 21.

Item 23. A compound represented by formula (12):

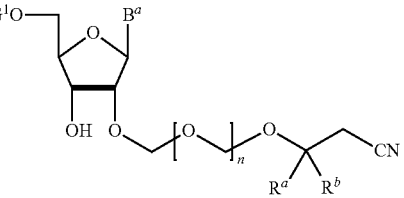

(12)

wherein

B$^a$, R$^a$, R$^b$ and n are the same as defined in Item 21, and G$^1$ represents a protecting group of a hydroxy group.

24. Use of the amidite compound of formula (1) in the production of RNA.

Effect of Invention

Use of the amidite compound of the present invention can conveniently prepare RNA with high purity in a solid phase synthesis.

MODE FOR CARRYING OUT THE INVENTION

Hereinafter, the present invention is explained in detail.

Here the expression of "comprise" as used herein encompasses the meanings of "essentially consist of" and "consist of".

The amidite compound of the present invention is characterized by formula (1).

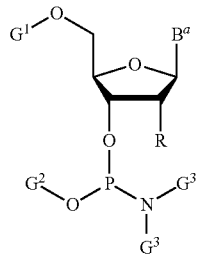

(1)

wherein R represents a formula:

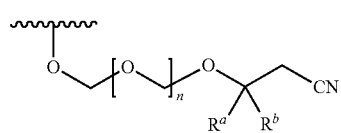

wherein
R$^a$ and R$^b$ are identical to or different from each other and each represents a methyl group, an ethyl group, or a hydrogen atom, with the proviso that R$^a$ and R$^b$ do not represent a hydrogen atom at the same time, n is an integer of 1 to 5, B$^a$ represents a group containing optionally-protected nucleobase structure, G$^1$ and G$^2$ are identical to or different from each other and each presents a protecting group for a hydroxy group, and G$^3$ are identical to or different from each other and each represents an alkyl group.

The nucleobase for B$^a$ is not particularly limited. Examples of the nucleobase include adenine, cytosine, guanine, uracil, thymine, 5-methylcytosine, pseudouracil, and 1-methylpseudouracil and the others. Also the nucleobase may be optionally substituted with any substituent(s). Examples of the substituent(s) include halogen atom, acyl group, alkyl group, arylalkyl group, alkoxy group, alkoxyalkyl group, cyanoalkyl group, hydroxy group, hydroxymethyl group, acyloxymethyl group, amino group, monoalkylamino group, dialkylamino group, carboxy group, cyano group, and nitro group, as well as any combinations of these two or more substituents.

When the nucleobase contains an exocyclic amino group, the protecting group for the amino group is not particularly limited, and any publicly known protecting groups which are used in a nucleic acid chemistry can be used. Examples of the substituent include methyl group, benzoyl group, 4-methoxybenzoyl group, acetyl group, propionyl group, butyryl group, isobutyryl group, phenylacetyl group, phenoxyacetyl group, 4-tert-butylphenoxyacetyl group, 4-isopropylphenoxyacetyl group, and (dimethylamino)methylene group, and the others, as well as any combinations of these two or more protecting groups.

More specifically, B$^a$ represents any of the below-mentioned formulae:

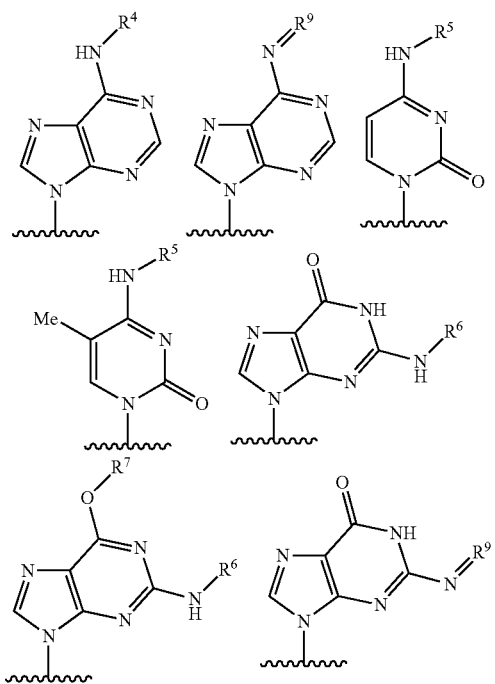

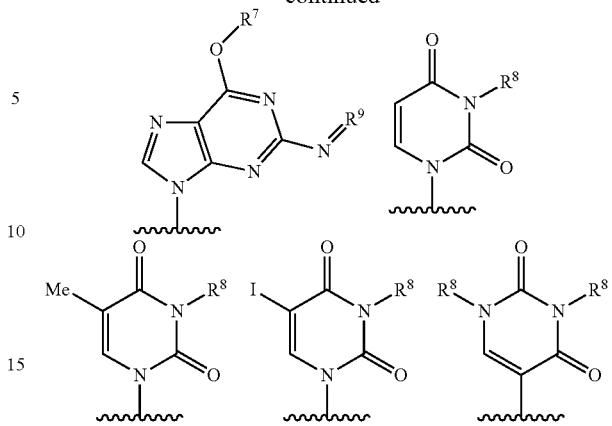

wherein R$^4$ represents a hydrogen atom, a methyl group, a phenoxyacetyl group, a 4-tert-butylphenoxyacetyl group, a 4-isopropylphenoxyacetyl group, a phenylacetyl group, an acetyl group or a benzoyl group, R$^5$ represents a hydrogen atom, an acetyl group, an isobutyryl group, or a benzoyl group, R$^6$ represents a hydrogen atom, a phenoxyacetyl group, a 4-tert-butylphenoxyacetyl group, a 4-isopropylphenoxyacetyl group, a phenylacetyl group, an acetyl group, or an isobutyryl group, R$^7$ represents a 2-cyanoethyl group, R$^8$ represents a hydrogen atom, a methyl group, a benzoyl group, a 4-methoxybenzoyl group, or a 4-methylbenzoyl group, R$^9$ represents a dimethylaminomethylene group.

G$^1$ can be used without particular limitations as long as it may function as a protecting group, and a publicly known protecting group used for an amidite compound can be used widely.

G$^1$ includes preferably the below-mentioned groups.

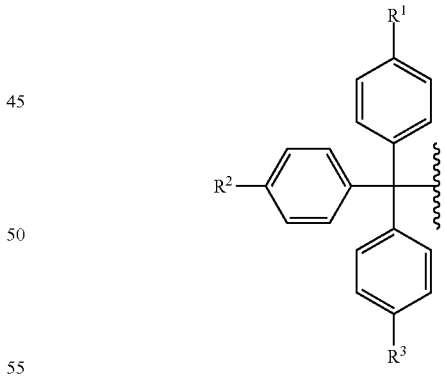

wherein R$^1$, R$^2$ and R$^3$ are identical to or different from each other and each represents a hydrogen atom or an alkoxy group.

With respect to R$^1$, R$^2$ and R$^3$, preferably, one of them represents a hydrogen atom, and the remaining two thereof represents an alkoxy group, and examples of the alkoxy group include particularly preferably a methoxy group.

G$^2$ can be used without particular limitations as long as it may function as a protecting group, and a publicly known protecting group for an amidite compound can be used widely. Examples of G$^2$ include a hydrogen atom, an alkyl group, an alkenyl group, an alkynyl group, a cycloalkyl group, a haloalkyl group, an aryl group, a heteroaryl group, an arylalkyl group, a cycloalkenyl group, a cycloalkylalkyl group, a cyclylalkyl group, a hydroxyalkyl group, an aminoalkyl group, an alkoxyalkyl group, a heterocyclylalkenyl group, a heterocyclyl alkyl group, a heteroarylalkyl group, a silyl group, a silyloxyalkyl group, a mono-, di- or tri-alkylsilyl group, a mono-, di- or tri-alkyl silyloxyalkyl group, a mono-, di- or tri-alkylsilyloxyalkyl group, and the others, and these groups may be optionally substituted with one or more electron-withdrawing groups.

$G^2$ includes preferably an alkyl group substituted with an electron-withdrawing group. Examples of the electron-withdrawing groups include cyano group, nitro group, alkylsulhonyl group, halogen atom, arylsulfonyl group, trihalomethyl group, trialkylamino group and the others, and preferably cyano group.

$G^2$ includes particularly preferably the below-mentioned groups.

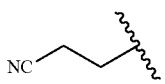

With respect to $G^3$, two $G^3$ may be combined each other to form a cyclic structure. It is preferred that both of $G^3$ represent an isopropyl group.

An alkyl group may be a straight or branched group, and includes preferably an alkyl group having 1 to 12 carbon atoms, more preferably an alkyl group having 1 to 6 carbon atoms. Examples of the alkyl group include methyl, ethyl, n-propyl, isoropyl, n-butyl, isobutyl, tert-butyl, n-pentyl, isopentyl, and hexyl. The alkyl group used herein includes an alkyl moiety such as alkoxy group.

$R^a$ represents preferably methyl. n is preferably an integer of 1 to 4, more preferably an integer of 1 to 3, further more preferably 1 or 2, and particularly 1.

Also the amidite compound of the present invention may be used in a free state or a salt state. Salts of the amidite compound of the present invention may be particularly limited, and include salts with inorganic bases (such as sodium salt, magnesium salt, potassium salt, calcium salt, aluminium salt); salts with organic bases such as methylamine, ethylamine, ethanolamine; salts with basic amino acids such as lysine, ornithine and arginine; and ammonium salts. The salt may be an acid addition salt, and examples of the salt include specifically acid addition salts with mineral acids such as hydrochloric acid, hydrobromic acid, hydroiodic acid, sulfuric acid, nitric acid, and phosphoric acid; organic acids such as formic acid, acetic acid, propionic acid, oxalic acid, malonic acid, maleic acid, tartaric acid, fumaric acid, succinic acid, lactic acid, maleic acid, citric acid, methanesulfonic acid, trifluoromethanesulfonic acid, and ethanesulfonic acid; and acidic amino acids such as aspartic acid and glutamic acid, and the others. The amidite compound of the present invention also includes salts, hydrates, solvates, and crystal polymorphs thereof.

The amidite compound of the present invention can be prepared according to the publicly known method such as those described in JP patent No. 5157168 B2 or JP patent No. 5554881 B2, the methods as below-mentioned in Examples, or the methods with added appropriate modifications to these methods as needed.

Also specific examples of the amidite compound of the present invention include any compounds listed in Table 1 of Examples.

The present invention encompasses an intermediate compound for preparation of the amidite compound represented by formula (1). The intermediate compound includes an ether compound represented by formula (4).

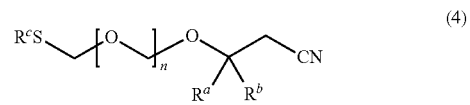

wherein
$R^a$ and $R^b$ are identical to or different from each other and each represents a methyl group, an ethyl group, or a hydrogen atom, with the proviso that $R^a$ and $R^b$ do not represent a hydrogen atom at the same time,
n is an integer of 1 to 5,
$R^c$ represents a C1-C6 alkyl group, or a phenyl group.

The ether compound represented by formula (4) can be prepared by reacting bis(alkylthiomethyl)ether or bis(phenylthiomethyl)ether with 3-hydroxy-3-alkylpropane nitrile in a solvent in the presence of an oxidizing agent and an acid.

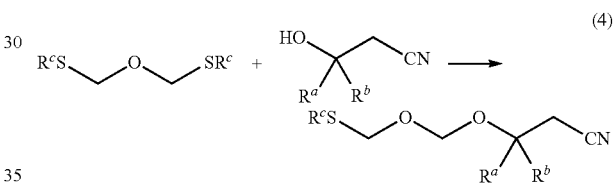

Bis(alkylthiomethyl)ether or bis(phenylthiomethyl)ether can be obtained, for example, as shown in the below-mentioned scheme, by reacting bischloromethylether or bis(aryloxymethyl) ether with the corresponding alkyl mercaptan or phenyl mercaptan. Examples of the bis(aryloxymethyl)ether include bis(2,4,6-trichlorophenyloxy methyl) ether.

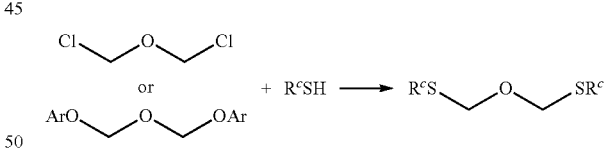

Also these compounds may be prepared according to the methods as below-mentioned in Examples, or the methods with added appropriate modifications to these methods as needed.

The step a and the step b for preparing the compound of formula (7) as one example of ether compound of formula (4) is explained.

The step a is explained.

Examples of the cyanide ions include cyanide ions derived from sodium cyanide, potassium cyanide, copper cyanide, and trimethylsilyl cyanide.

When the trimethylsily cyanide is used, a base is preferably added.

Examples of the base in this reaction include alkali metal hydroxide, alkaline earth metal hydroxide, and ammonium hydroxide, as well as any combinations of these two or more bases. In the present invention, lithium hydroxide or lithium hydroxide monohydrate is preferably used. The amount of the base is within a range of usually 0.01 to 1 equivalent, and preferably 0.1 to 0.3 equivalent to 1 equivalent of epoxy compound represented by formula (5).

The amount of the cyanide ion is within a range of usually 0.3 to 2 equivalents, and preferably 0.6 to 0.8 equivalent to 1 equivalent of the compound represented by formula (5).

The reaction temperature of this reaction is within a range of usually −20 to 40° C., and preferably 0 to 35° C. The reaction duration of this reaction is within a range of usually 0.5 to 24 hours, and preferably usually 1 to 5 hour(s).

The step b is explained below.

Examples of the oxidizing agent include N-halogenated succinimide such as N-chlorosuccinimide, N-bromosuccinimide, N-iodosuccinimide, and N-halogenated hydantoin such as 1,3-diiodo-5,5-dimethyl hydantoin, and halogens such as chlorine, bromine and iodine, and any combinations of two or more of them. In the present invention, N-halogenated succinimide is preferably used, and N-iodosuccinimide is more preferably used.

An acid is not particularly limited, and includes, for example, perfluoroalkyl carboxylic acid and salts thereof, perfluoroalkylsulfonic acid and salts thereof, and alkylsulfonic acid and salts thereof, as well as any combinations of two or more of them. Examples of salts include for example, copper salts and silver salts. Specific examples of the acid include methanesulfonic acid, paratoluenesulfonic acid, camphor sulfonic acid, trifluoromethanesulfonic acid, and silver trifluoromethanesulfonate, as well as any combinations of these two or more acids. In the present invention, trifluoromethanesulfonic acid is preferably used.

Examples of solvents include tetrahydrofuran, 2-methyltetrahydrofuran, cyclopentyl methyl ether, dioxane, dichloromethane, and toluene, as well as any combinations of these two or more solvents. In the present invention, tetrahydrofuran is preferably used.

The amount of 3-hydroxyalkyl nitrile is within a range of usually 0.5 to 2.0 equivalents and preferably 0.8 to 1.5 equivalents as opposed to 1 equivalent of bis(alkylthiomethyl)ether or bis(phenylthiomethyl)ether. The amount of the oxidizing agent is within a range of usually 0.5 to 2 equivalents, and preferably 0.7 to 1.2 equivalents as opposed to 1 equivalent of bis(alkylthiomethyl)ether or bis(phenylthiomethyl)ether. The amount of the acid is within a range of usually 0.001 to 2.0 equivalents, and preferably 0.01 to 0.1 equivalents as opposed to 1 equivalent of bis(alkylthiomethyl)ether or bis(phenylthiomethyl)ether.

The reaction temperature of this reaction is within a range of usually −80 to 0° C., and preferably −50 to −30° C. The reaction duration of this reaction is within a range of usually 1 to 24 hours, and preferably 2 to 6 hours.

The completion of the reaction can be confirmed by sampling a part of the reaction mass, followed by analysis method such as GC, TLC, and LC and so on. After a completion of the reaction, a base such as triethylamine and so on may be added to a reaction mass to quench the reaction. The reaction mass is poured into water, and subjected to usual working up treatments such as extraction with organic solvents, washing, and concentrations, and the others to obtain the residues containing the ether compound represented by formula (7). The residues can be subjected to a purification procedure such as distillation and chromatography and so on to obtain the ether compound represented by formula (7) with high purity.

In the embodiment, preferably $R^a$ represents a methyl group or an ethyl group, $R^b$ represents a hydrogen atom, and $R^c$ represents a methyl group. More preferably, $R^a$ represents a methyl group, $R^k$ represents a hydrogen atom, and $R^c$ represents a methyl group.

The compounds described herein can be prepared by the below-mentioned methods.

Among these compounds, the compound of formula (8) can be prepared according to the preparation method comprising the below-mentioned steps A to C.

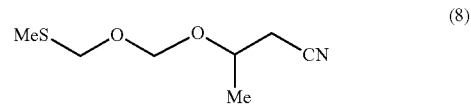 [SMILES: CSCOCOC(C)CC#N]

(8)

Step A: a step of hydrolyzing 3-aminocrotononitrile;
Step B: a step of reducing the cyanoacetone obtained in the step A; and
Step C: a step of reacting 3-hydroxybutanenitrile obtained in the step B with bis(methylthiomethyl)ether in a solvent in the presence of an oxidizing agent and an acid.

Step A:

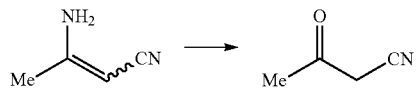 [SMILES: CC(N)=CC#N ; CC(=O)CC#N]

In this reaction, 3-aminocrotononitrile can be hydrolyzed to obtain cyanoacetone.

A hydrolysis can be conducted, for example, by mixing 3-aminocrotononitrile and an acid in the presence of water. Examples of the acid may be hydrous acid or anhydrous acid, and include hydrochloric acid, sulfuric acid, and methanesulfonic acid, and so on. In the present invention, hydrochloric acid is preferably used. In this reaction, when acid anhydride is used as an acid, the reaction is conducted in the presence of water by adding water, or when a hydrous acid is used as an acid, water may be added or not.

An amount of the acid is within a range of usually 1 to 10 equivalent(s) and preferably 1 to 1.5 equivalent(s), as opposed to 1 equivalent of 3-aminocrotononitrile.

The reaction temperature of this reaction is within a range of usually −20 to 100° C., and preferably 0 to 85° C. The reaction duration of this reaction is within a range of usually 1 to 24 hour(s), and preferably 1 to 4 hour(s).

Step B:

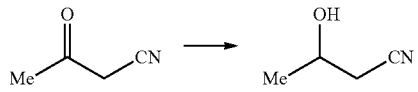 [SMILES: CC(=O)CC#N ; CC(O)CC#N]

Examples of the reducing agent used in the reduction step of the step B include metallic reducing agent such as sodium borohydride.

An amount of the reducing agent is within a range of usually 0.25 to 2 equivalents and preferably 0.5 to 1 equivalent(s), as opposed to 1 equivalent of cyanoacetone.

This reaction can be conducted in a solvent, and examples of the solvent include ether solvents such as tetrahydrofuran, 2-methyltetrahydrofuran, tetrahydropyran, 4-methyltetrahydropyran, cyclopentyl methyl ether, and dioxane; alcoholic solvents such as methanol and ethanol, as well as any combinations of these two or more solvents. In the present invention, tetrahydrofuran is preferably used.

Also this reduction step can be also conducted by a biological method using a yeast.

The reaction temperature is within a range of usually −20 to 60° C. and preferably 0 to 35° C. The reaction duration of this reaction is within a range of 0.5 to 24 hours, and preferably 1 to 4 hour(s).

Step C:

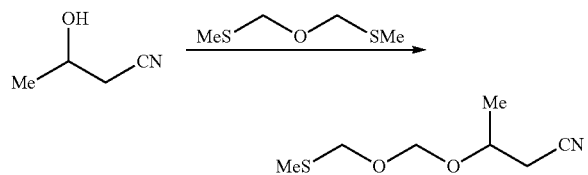

The reaction of the step C can be conducted by reacting an alcohol with bis(methylthiomethyl)ether in the presence of an oxidizing agent (such as halogenating agent). Examples of the halogenating agent include N-halogenated succinimide such as N-chlorosuccinimide, N-bromosuccinimide, and N-iodosuccinimide; N-halogenated hydantoin such as 1,3-diiodo-5,5-dimethyl hydantoin, and halogens such as chlorine, bromine and iodine. In the present invention, N-halogenated succinimide is preferably used, and N-iodosuccinimide is more preferably used.

The kind of the acid to be used in this reaction is not particularly limited, and for example, include perfluoroalkylcarboxylic acid and salts thereof, perfluoroalkylsulfonic acid and salts thereof, as well as alkylsulfonic acid and salts thereof. Examples of the salt include copper salts and silver salts. Specific examples of the acid include methanesulfonic acid, paratoluenesulfonic acid, trifluoromethanesulfonic acid, silver trifluoromethansulfonate and the others. In the present invention, trifluoromethanesulfonic acid is preferably used.

Examples of the solvents include tetrahydrofuran, 2-methyl tetrahydrofuran, tetrahydropyran, 4-methyl tetrahydropyran, cyclopentyl methyl ether, dioxane, dichloromethane, toluene and the others. In the present invention, tetrahydrofuran is preferably used.

An amount of 3-hydroxybutanenitrile is within a range of usually 0.5 to 2.0 equivalents and preferably 0.8 to 1.5 equivalents to 1 equivalent of bis(methylthiomethyl)ether. The amount of the oxidizing agent is within a range of usually 0.5 to 2.0 equivalents and preferably 0.7 to 1.2 equivalents to 1 equivalent of bis(methylthiomethyl)ether. An amount of the acid is within a range of usually 0.001 to 2.0 equivalents and preferably 0.01 to 0.1 equivalents to 1 equivalent of bis(methylthiomethyl)ether.

The reaction temperature of this reaction is within a range of usually −80 to 0° C., and preferably −50 to −30° C. The reaction duration of this reaction is within a range of usually 1 to 24 hour(s), and preferably 2 to 6 hours.

The completion of the reaction can be confirmed by sampling a part of the reaction mass, followed by analysis method such as GC, TLC, and LC and so on. After a completion of the reaction, a base such as triethylamine and so on may be added to a reaction mass to quench the reaction. The reaction mass is poured into water, and subjected to usual working up treatments such as extraction with organic solvents, washing, and concentrations, and the others to obtain the residues containing the ether compound represented by formula (8). The residues can be subjected to a purification procedure such as distillation and chromatography and so on to obtain the ether compound represented by formula (8) with high purity.

The amidite compound of the present invention can be used as a raw material for preparing RNA in the solid phase synthesis. Use of the amidite compound of the present invention in the solid phase synthesis method can prepare RNA with high purity.

The method for preparing the compound containing polynucleotide structure represented by the following formula (2) of the present invention is characterized by comprising a step of reacting the amidite compound in a solid phase synthesis.

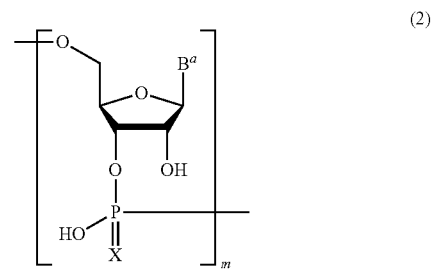

(2)

wherein $B^a$ is identical to or different from each other and each represents a group containing optionally-protected nucleobase structure, X represents an oxygen atom or a sulfur atom, and m is a positive integer.

Also, the preparation method of the present invention may also comprise a step of treating the compound containing oligonucleotide structure represented by formula (3) with tetraalkyl ammonium fluoride to obtain the compound containing oligonucleotide structure represented by formula (2).

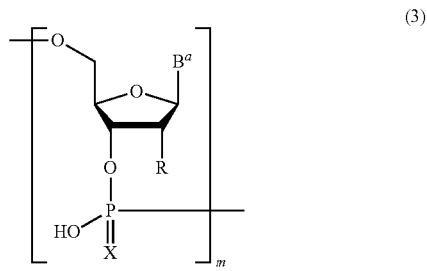

(3)

wherein $B^a$ is identical to different from each other and each represents a group containing an optionally protected nucleobase structure, X represents an oxygen atom or a sulfur atom, and R is identical to or different from each other and each represents a formula:

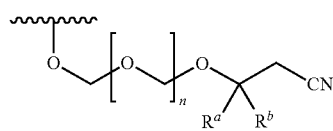

wherein
R$^a$ and R$^b$ are identical to or different from each other and each represents a methyl group, an ethyl group or a hydrogen atom, with the proviso that R$^a$ and R$^b$ do not represent a hydrogen atom at the same time, and
n is a positive integer,
m is a positive integer.

B$^a$ and m in the formula (2) and the formula (3) are the same as defined in formula (1).

m is not particularly limited, and is preferably an integer of 2 to 300.

The term of "compound containing polynucleotide structure" as used herein represents a compound containing at least one RNA, and preferably the compound consisting of only RNA.

A solid phase synthesis can be conducted according to a publicly known method such as phosphoramidite method (for example, a method described in JP patent No. 5157168 B2 and JP Patent No. 5554881 B2). Also the solid phase synthesis can be conducted with a commercially available automatic synthesizer for nucleic acid, and the other apparatuses.

A method for preparing the compound containing polynucleotide structure represented by formula (2) comprises specifically (A) a step of deprotecting a hydroxy group at 5' position of the first amidite compound that is supported on a solid support (for example, G$^1$ in the formula (1)); (B) a step of condensing the deprotected amidite compound which is formed in the step (A) with the second amidite compound; (C) an optional step of capping a hydroxy group at 5' position of unreacted compound in the step (B); (D) a step of converting a phosphite group in a condensed compound which is formed in the step (B) or (C) to a phosphate group or a thiophosphate group; (E) a step of cutting out the compound obtained in the step (D) and deprotecting the hydroxy group at 2' position and nucleobase; and (F) a step of deprotecting the hydroxy group at 5' position. The steps (A) to (D) are repeated to prepare the compound containing polynucleotide structure having the desired strength chain (for example, the compound of formula (3)).

The compound containing oligonucleotide structure represented by formula (3) may be preferably treated with tetraalkyl ammonium fluoride to leave the protecting group at 2' position, and to prepare the compound containing oligonucleotide structure represented by formula (2). The reaction condition for the reaction (for example, reaction temperature, reaction duration, amounts of reagent(s)) may adopt the condition according to the publicly known method.

The compound containing oligonucleotide structure represented by formula (2) which is obtained by the preparation method of the present invention may be conducted by an isolation and a purification. Usually, RNA can be usually isolated by using a precipitation method, an extraction method, and a purification method. Specifically it is adopted a method of adding any solvent with low solubility against RNA, such as ethanol and isopropyl alcohol to the solution after the reaction to precipitate RNA, and a method of adding a solution of phenol/chloroform/isoamyl alcohol (such as phenol/chloroform/isoamyl alcohol=25/24/1) to the reaction solution to back extract RNA into an aqueous layer. Thereafter, the resulting RNA can be isolated or purified by a manner of a publicly known high performance liquid chromatography (HPLC) such as reverse-phase column chromatography, anion exchange column chromatography, and affinity column chromatography.

According to the preparation method of the present invention, it can be prepared RNA with higher purity than a conventional one.

The reaction conditions for preparing the amidite compound of the present invention and the ether compound represented by formula (4) are not particularly limited. The ether compound represented by formula (4) can be synthesized using a flow reactor.

In order to reduce the impurity contained in the amidite compound of the present invention, a reduction step with hydrogen gas or a reduction step with magnesium in the presence of a transition metal catalyst such as palladium.

3-Hydroxybutanenitrile can be also synthesized via the below-mentioned preparation route using lactic acid or acetaldehyde as raw material by referring to the Reference 1: Chemical Communications, 2011, 47, (12), 3613, the Reference 2: Applied Microbiology and Biotechnology, 2016, 100, (3), 1241, the Reference 3): Journal of Organic Chemistry, 2010, 75(21), 7092, and the Reference 4): Chinese Patent No. CN 107602497 B2.

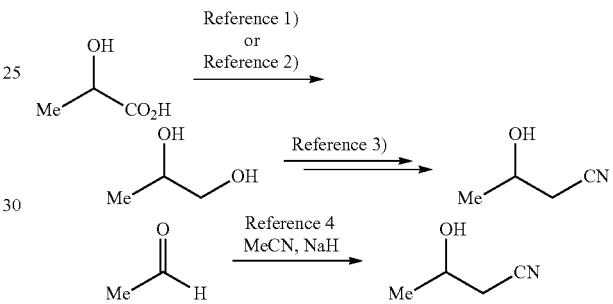

The compound of formula (1) can be prepared from the compound of formula (9) by the steps 1, 2, 3 and 4 in the below-mentioned scheme 1.

In the compound of formula (9), B$^a$ has the same meaning as the aforementioned one, and G$^4$ has typically the below-mentioned G$^4$-1 or G$^4$-2 structure.

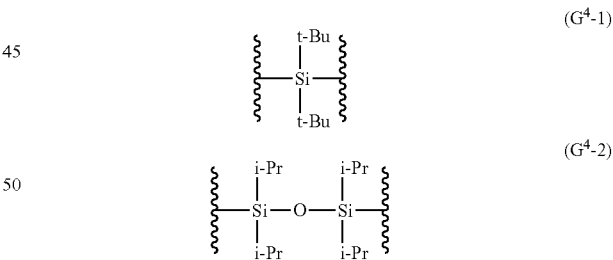

These compounds can be purchased as a commercially available products, or can be prepared according to the method described in Tetrahedron Letters, 2005, 46, 2961, for example.

Step 1 (Ether Conversion Step)

The ether conversion step is conducted by reacting the compound of formula (9) with the compound of formula (4). This reaction is usually conducted by adding an oxidizing agent. The oxidizing agent used in this step is not particularly limited, and is preferably at least one compound selected from the group consisting of N-chlorosuccinimide, N-bromosuccinimide, N-iodosuccinimide, iodine, 1,3-diiodo-5,5'-dimethylhydantoin, bromine and choline.

In this step, an acid may be added, and the acid used is not particularly limited, and is preferably at least one compound selected from the group consisting of perfluoroalkylcarboxylic acid, pefluoroalkylsulfonic acid, alkylsulfonic acid, and salts thereof.

The reaction solvent used in this step is not particularly limited, and includes for example, ethers such as diethyl ether, THF (tetrahydrofuran), 2-methyl tetrahydrofuran, tetrahydropyran, 4-methyltetrahydropyran, dimethoxyethane, diglyme, cyclopentyl methyl ether, and dioxane; nitriles such as acetonitrile; aromatic hydrocarbons such as toluene, chlorobenzene, and dichlorobenzene; dichloromethane; as well as any combinations of two or more of the solvents. Preferred examples of the solvents include diethyl ether, THF (tetrahydrofuran), 2-methyltetrahydrofuran, tetrahydropyran, 4-methyltetrahydropyran, dimethoxyethane, diglyme, cyclopentyl methyl ether, and dioxane. More preferred solvents include tetrahydropyran, and 4-methylhydropyran.

The reaction duration in this step is not particularly limited, and is, for example, within a range 10 minutes to 12 hours, and preferably 10 minutes to 6 hours.

The reaction temperature in this step is not particularly limited, and is, for example, within −80 to −30° C., and preferably −60 to −10° C.

In this step, the concentration of the ether compound represented by the formula (4) is not particularly limited, and may be set as needed.

In this step, number of moles of the ether compound represented by the formula (4) is, for example, within a range of 0.5 to 2 times, and preferably 0.8 to 1.5 times, to 1 mole of the compound represented by formula (9).

In this step, number of moles of the oxidizing agent is, for example, within a range of 0.5 to 10 times, and preferably 0.8 to 6 times, to 1 mole of the compound represented by formula (9).

Step 2 (Deprotection Step)

The compound of formula (10) which is obtained in the step 1 is subjected to a deprotection reaction to convert into the compound of formula (11). The deprotection step can be conducted according to a publicly known method, and typically, can be deprotected by treating with hydrogen fluoride/triethylamine or hydrogen fluoride/pyridine, in a solvent.

Step 3 (Protection Step of 5' Hydroxy Group)

The compound of formula (11) which obtained in the step is subjected to a protection step, and the introduction of the protecting group can be conducted according to a publicly known method, typically by reacting the compound (11) with 4,4'-dimethoxytritylchloride in a pyridine to prepare the compound (12).

Step 4 (Amidite Step)

The step is conducted by reacting the compound of formula (12) which is obtained in the step above with the compound of formula (13). Typically, the reaction is conducted by reacting 2-cyanoethyl-N,N,N',N'-tetraisopropylphosphorodiamidite as the compound of formula (13) in the presence of diisopropyl ammonium tetrazolide. The reaction of amidite can be conducted according to the method described in Examples 2 to 5 of Japanese patent No. 5554881 B2.

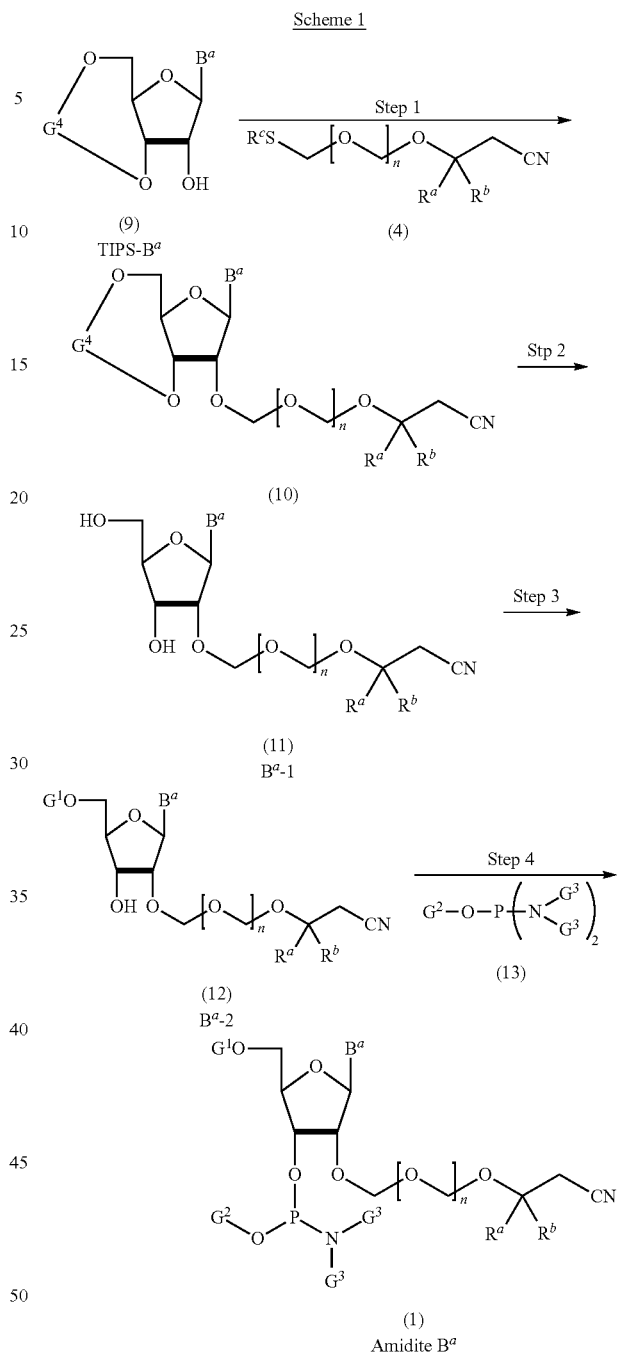

Scheme 1

As explained above, the compounds of formulae (9), (10), (11) and (12) can be used in the preparation of the amidite compound of formula (1). According to the preferred embodiment of the compound, n is 1.

EXAMPLES

Hereinafter, Examples are described to explain the present invention in more detail. The present invention is not however limited to these examples and so on.

Hereinafter, the following abbreviations are used herein.
PMM=((1-cyanopropan-2-yl)oxy)methoxy)methyl group,
BMM=((1-cyanobutan-2-yl)oxy)methoxy)methyl group, TBM=((1-cyano-2-methylpropan-2-yl)oxy)methoxy)
    methyl group,
PMM2=((2-cyanopropoxy)methoxy)methyl group,
CPM=((1-cyanopropan-2-yl)oxy)methyl group,
A=adenine, G=guanine, C=cytosine, U=uracil.

Preparation of PMM Amidite

Preparation Example 1

1) Preparation of 3-hydroxybutanenitrile

To propylene oxide (12.4 g, 0.21 mmol) was added lithium hydroxide monohydrate (1.8 g, 42.8 mmol), and the mixture was cooled to 4° C., and thereto was then added dropwise trimethylsilyl cyanide (15.5 g, 0.15 mol) slowly. After the dropwise addition was completed and several tens of minutes were passed, the inner temperature was raised to 35° C. The mixture was stirred in ice bath (inner temperature 5° C.) for 30 minutes, at 10 to 15° C. for 1 hour, and further at room temperature (25° C.) for 30 minutes. To the reaction solution was added water (15 mL) and the mixture was stirred at room temperature for 30 minutes. Then the mixture was extracted with diethyl ether (50 mL×three (3) times), washed with saturated saline, and dried over anhydrous sodium sulfate, and the solvents were then distilled off to obtain crude 3-hydroxybutanenitrile as colorless and transparent liquid 10.6 g (yield 84%).

2) Preparation of a PMM Reagent

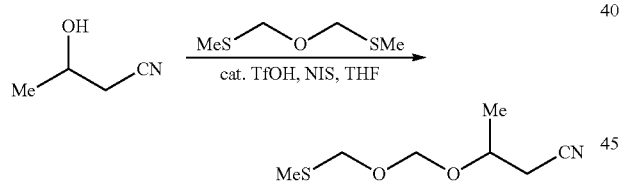

Bis(methylthiomethyl)ether (32.41 g, 0.234 mol, 2.0 eq.) was solubilized in dry THF (300 mL), and thereto was added molecular sieves 4A (32 g), and the mixture was stirred for 10 minutes. The mixture was cooled to −50° C., and thereto were added trifluromethanesulfonic acid (TfOH) (0.88 mL, 5.85 mmol, 0.05 eq.) and N-iodosuccinimide (NIS) (31.5 g, 0.140 mol, 1.2 eq.), and thereto was added dropwise crude 3-hydroxybutanenitrile (10 g, 0.117 mmol), and the mixture was stirred at around −50 to −45° C. for 2 hours. To the reaction solution were added saturated aqueous sodium sulfite solution (150 mL), saturated sodium hydrogen carbonate solution (150 mL) and ethyl acetate (300 mL), and the mixture was stirred at 0 to 10° C. for 10 minutes. After separating the mixture with a separatory funnel, an organic layer was washed with saturated brine (150 mL), dried over anhydrous magnesium sulfate, and the solvents were distilled off under reduced pressure. The residue was subjected to a silica gel column chromatography (Hexane/AcOEt=10/1 to 5/1, silica 800 mL) to obtain the PMM reagent as yellow liquid 5.9 g (Yield 28%). As a result of the GC/FID analysis on a purity of the product, the purity was showed 97.2%.

PMM Reagent

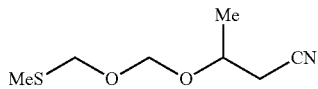 [SMILES: CSCOCOC(C)CC#N]

Pale Yellow Transparent Liquid $^1$H-NMR (CDCl$_3$): δ 4.93-4.84 (m, 2H) 4.75 (s, 2H) 4.06-4.00 (m, 1H) 2.57 (t, 2H), 2.17 (s, 3H) 1.35 (d, 3H)

Here the method for preparing bis(methylthiomethyl) ether is referred to JP 2016-50203 A1.

Preparation Example 2

1) Preparation of Cyanoacetone

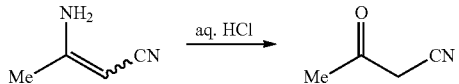

3-Aminocrotononitrile (50 g, 0.609 mol) and 6N hydrochloric acid (143 mL) were mixed, and the mixture was stirred in a bath of 60° C. for 1 hour, and then allowed to cool to room temperature, and the precipitates were removed by filtration. After the reaction solution was extracted with dichloromethane (250 mL), the organic layer was dried over magnesium sulfate. After the solvent was distilled off with an evaporator, the precipitates were removed by filtration, and dried with a vacuum pump to obtain cyanoacetone (41.4 g, yield 81%, GC purity 99.4%).

2) 3-Hydroxybutanenitrile

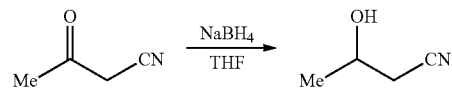

To THF (207 mL) was added sodium borohydride (11.35 g, 0.30 mol), and the mixture was cooled in ice bath, and then thereto was added dropwise a solution of cyanoacetone (41.4 g, 0.50 mol) in THF (41 mL) (inner temperature 0 to 8° C., dropwise addition time 35 minutes). After the mixture was further stirred under ice bath for 30 minutes, thereto was added water (100 mL), and the mixture was extracted with ethyl acetate (200 mL). After the organic layer was treated with saturated brine and dried over magnesium sulfate, the precipitated solids were removed by filtration. The solvents were distilled with rotary evaporator and vacuum pump to obtain yellow liquid (38 g). The obtained liquids were purified by distillation under reduced pressure (70 to 80 Pa, bath temperature 70° C.) to obtain 3-hydroxybutanenitrile (29.5 g, yield 69.5%, GC purity 99.1%).

3) Preparation of PMM Reagent

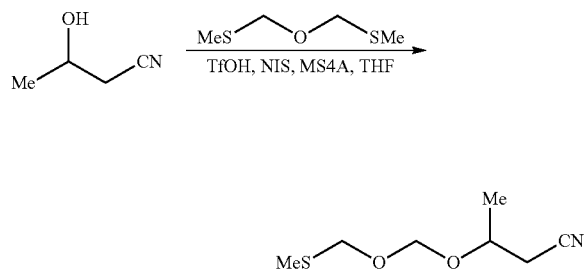

Bismethylthiomethyl ether (7.45 g, 53.9 mmol), molecular sieves 4A (7.5 g) and THF (111 mL) were mixed, and after cooling (−60 to −55° C.), thereto were added N-iodosuccinimide (NIS) (14.4 g, 1.19 equiv.), trifluoromethanesulfonic acid (TfOH) (143 μL, 0.030 equiv.), and 3-hydroxybutanenitrile (5.0 g, 1.09 equiv.). After the mixture was stirred at −50 to −45° C. for 4 hours, thereto was added dropwise triethylamine (5.1 mL). The reactor was immersed into water bath and the reaction solution was raised to around 10° C., and thereafter, the reaction solution was poured into an aqueous solution prepared in advance at 10° C. (a mixture of sodium thiosulfate pentahydrate 21.8 g, sodium bicarbonate 7.7 g, and water 165 mL). Thereto was added ethyl acetate (50 mL), and the mixture was stirred at 10 to 15° C. for 30 minutes, and after the mixture was filtered through Celite (7.5 g), the mixture was separated with a separatory funnel, and the organic layer was washed with saturated brine (30 mL), dried over magnesium sulfate (3.8 g), and concentrated with rotary evaporator to obtain crude product (11.5 g, GC purity 49.8%). The product was purified with a silica gel column chromatography (silica gel 300 mL, hexane/ethyl acetate=10/1) to obtain 3-((methylthio methoxy)methoxy)butane nitrile (pale yellow transparent liquid, 5.32 g, yield 56%, purity 99.5%).

Preparation Examples 3 to 8 (Preparation of Protecting Reagent at 2' Position)

In a similar manner as in the Examples above, a (R)-PMM reagent, a (S)-PMM reagent, a BMM reagent, a TBM reagent, and a PMM2 reagent were prepared. Also a CPM reagent was prepared according to the following method.

Preparation Example 3

(R)-PMM Reagent (Prepared from (R-(+)-Propylene Oxide Purchased from Sigma Aldrich Co. LLC)

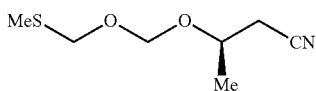 [SMILES: CSCOCO[C@H](C)CC#N]

Pale Yellow Transparent Liquid
¹H-NMR (CDCl₃): δ 4.92 (d, 1H) 4.85 (d, 1H) 4.75 (s, 2H) 4.03 (m, 1H) 2.57 (m, 2H) 2.17 (s, 3H) 1.35 (d, 3H)

Preparation Example 4

(S)-PMM Reagent (Prepared from (R-(−)-Propylene Oxide from Sigma Aldrich Co. LLC)

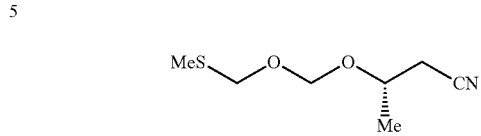

Pale Yellow Transparent Liquid
¹H-NMR (CDCl₃): δ 4.92 (d, 1H) 4.85 (d, 1H) 4.75 (s, 2H) 4.03 (m, 1H) 2.57 (m, 2H) 2.17 (s, 3H) 1.34 (d, 3H)

Preparation Example 5

BMM Reagent

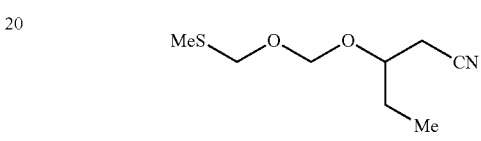

Pale Yellow Transparent Liquid
¹H-NMR (CDCl₃): δ 4.95 (d, 1H) 4.84 (d, 1H) 4.76 (s, 2H) 3.79 (m, 1H) 2.60 (m, 2H) 2.17 (s, 3H) 1.70 (m, 2H) 0.97 (t, 3H)

Preparation Example 6

TBM Reagent

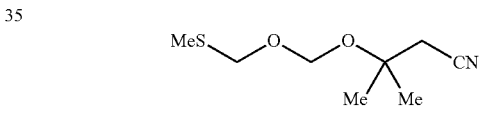

Pale Yellow Transparent Liquid
¹H-NMR (CDCl₃): δ 4.94 (s, 2H) 4.77 (s, 2H) 2.58 (s, 2H) 2.16 (s, 3H) 1.42 (s, 3H)

Preparation Example 7

PMM2 Reagent

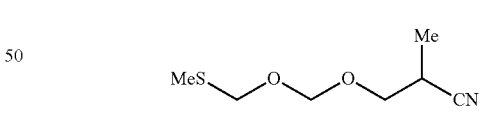

Pale Yellow Transparent Liquid
¹H-NMR (CDCl₃): δ 4.86 (s, 2H) 4.73 (s, 2H) 3.71-3.61 (m, 2H) 2.94-2.87 (m, 1H) 2.18 (s, 3H) 1.35 (d, 3H)

Preparation Example 8

Preparation of CPM Reagent
In a 2000 mL round-bottom flask, 51.0 g (600 mmol) of 3-hydroxybutanenitrile (3-HBN), 640 mL (9 mol) of dimethyl sulfoxide were placed, and thereto were added 350 mL (6.1 mol) of acetic acid and 600 mL (6.3 mmol) of acetic anhydride. The mixture was stirred under nitrogen gas atmosphere at room temperature for 15 minutes, and the mixture was then heated in oil bath (50° C.) for 12 hours with stirring. The disappearance of the raw material 3-HBN was confirmed by GC, and the mixture was then allowed to cool to room temperature. 1600 g (19.5 mol) of sodium bicarbonate suspended in 8 L of deionized water, and thereto was added the above resulting reaction solutions gradually. After foaming ceased, the reaction mixture was transferred into a separatory funnel, and extracted with 500 mL of ethyl acetate. The organic layer was washed with 1 L of deionized water, dried over magnesium sulfate, and concentrated under reduced pressure to obtain 91.0 g of pale yellow brown oil.

The oil was purified with a silica gel column (a slurry was prepared from $SiO_2$ 1000 ml and n-hexane:AcOEt=20:1, and packed into the column). The sample was charged on the column, and eluted with n-Hexane:AcOEt=20:1. After 1000 mL was eluted, 200 mL (15 sets) were collected. After eluted with Hexane:AcOEt=3:1, 200 mL (15 sets) were collected. The fractions containing the products were combined and concentrated under reduced pressure, and dried through vacuum line under reduced pressure. 53.28 g of colorless oil was obtained.

A CPM Reagent

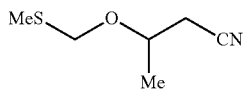

Pale Yellow Transparent Liquid
$^1$H-NMR (CDCl$_3$): δ 4.72 (d, 1H) 4.64 (d, 1H) 4.15 (m, 1H) 2.56 (m, 2H) 2.20 (s, 3H) 1.31 (d, 3H)

Preparation of Amidite

Preparation Example 9

A preparation example of PMM amidite U wherein a nucleobase moiety is uracil is shown below.

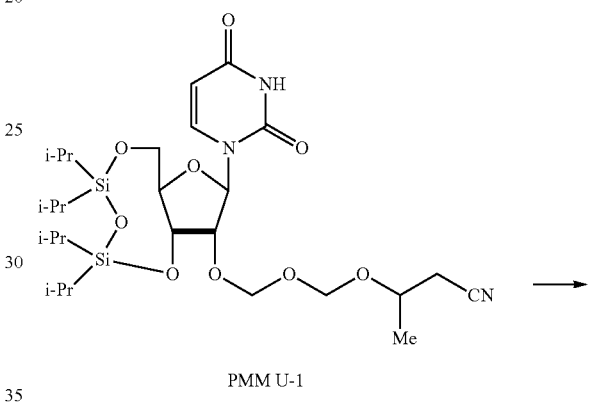

TIPS-U

TIPS-U (20.0 g), THF (40 mL) and toluene (60 mL) were placed in a reactor, and the mixture was concentrated to 74 mL and dehydrated. The reaction solution was cooled to −50° C., and thereto were added dropwise a solution of the PMM reagent (10.80 g), TfOH (12.48 g), and NIS (12.4 g)/THF (26 mL). After the mixture was stirred at −50° C. for 2 hours, the reaction solution was poured into an ice-cooled solution of sodium hydrocarbonate (7.0 g) and sodium thiosulfate (20.0 g)/water (130 mL), and the mixture was separated with a separatory funnel at room temperature. Thereafter, the mixture was washed with sodium hydrogen carbonate (3.5 g) and sodium thiosulfate (10.0 g)/water (65 mL). The organic layer was concentrated to obtain a crude product containing the desired compound. Exact Mass: 613.3, Actual Mass: 612.3 (ESI (−)).

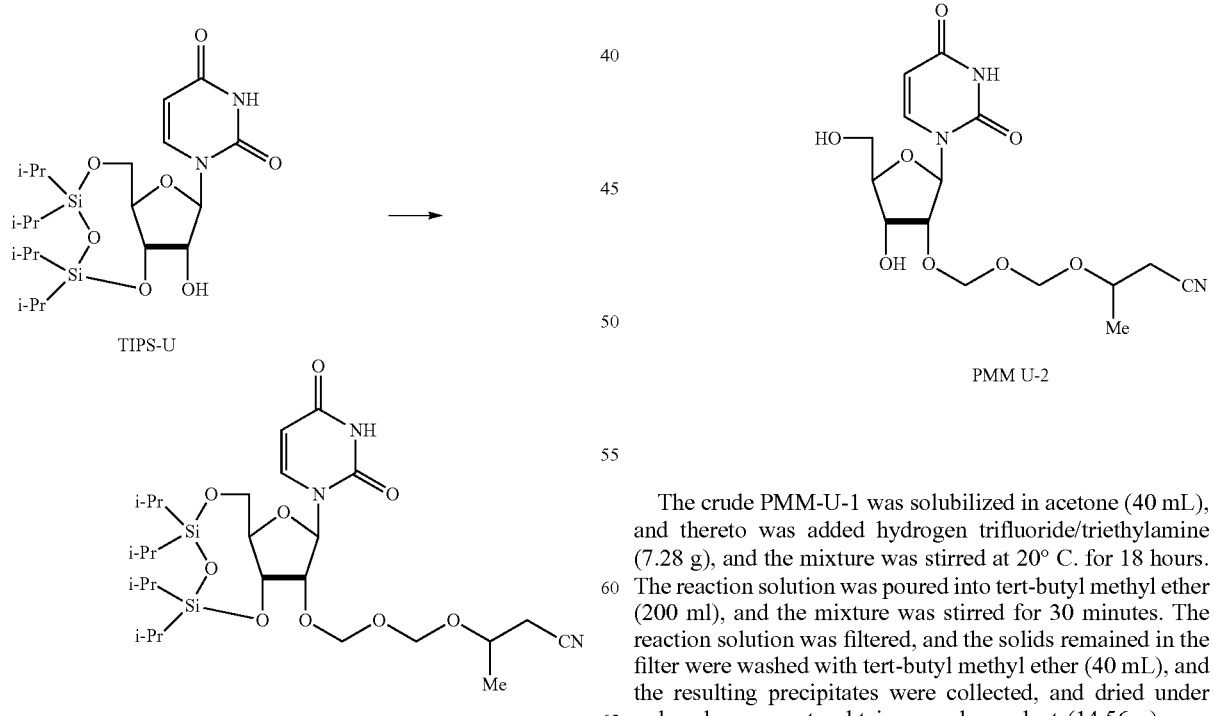

PMM U-1

PMM U-2

The crude PMM-U-1 was solubilized in acetone (40 mL), and thereto was added hydrogen trifluoride/triethylamine (7.28 g), and the mixture was stirred at 20° C. for 18 hours. The reaction solution was poured into tert-butyl methyl ether (200 ml), and the mixture was stirred for 30 minutes. The reaction solution was filtered, and the solids remained in the filter were washed with tert-butyl methyl ether (40 mL), and the resulting precipitates were collected, and dried under reduced pressure to obtain a crude product (14.56 g) containing the desired product. Exact Mass: 371.1, Actual Mass: 370.2 (ESI (−)).

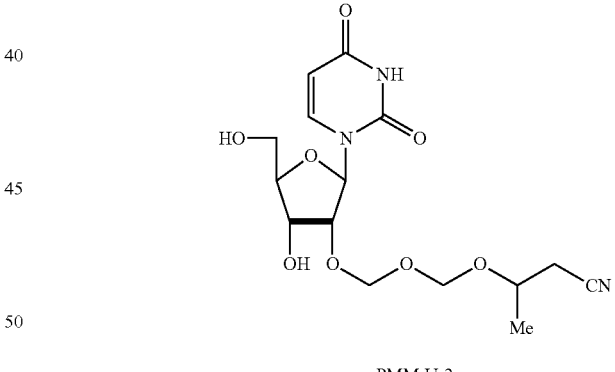

PMM U-1

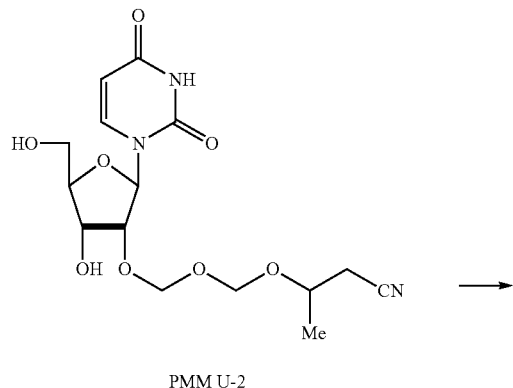

PMM U-2

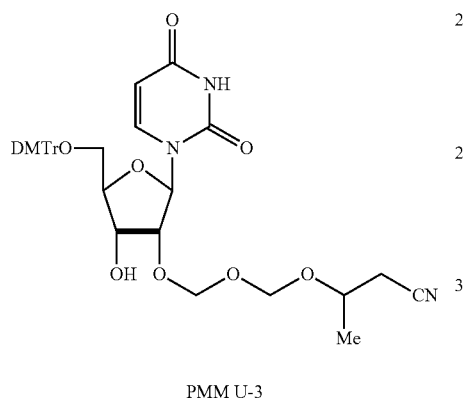

PMM U-3

The crude PMM-U-2 (14.5 g), pyridine (72.5 ml) and acetonitrile (29 mL) and toluene (72.5 mL) were placed in a reactor vessel and ice-cooled. To the mixture was added 4,4'-dimethoxytritylchloride (15.86 g) and the mixture was stirred at room temperature for 4 hours. Thereafter, thereto were added methanol (7.2 mL) and toluene (29 mL), and the mixture was washed with 5% aqueous sodium hydrogen carbonate solution (43.5 mL) twice and 10% aqueous sodium chloride solution (43.5 mL) once. Thereafter, the organic layer was concentrated. The concentrates were purified by a silica gel column chromatography to obtain the desired product (21.12 g). Exact Mass: 673.3, Actual Mass: 672.3 (ESI (−)).

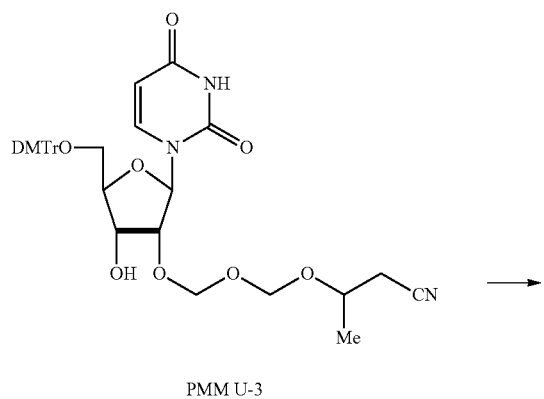

PMM U-3

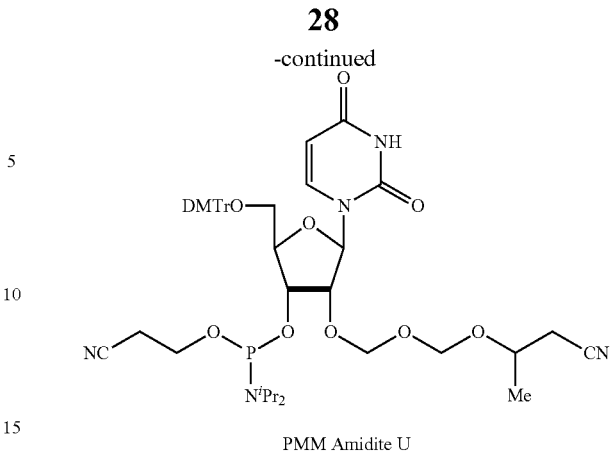

PMM Amidite U

PMM-U-3 (20.0 g), acetonitrile (60 mL), diisopropyl ammonium tetrazolide (5.88 g), and 2-cyanoethyl-N,N,N',N'-tetraisopropyl phosphorodiamidite (10.75 g) were placed in a reactor, and the mixture was stirred at 35° C. for 4 hours. To the reaction solution was added toluene (200 mL), and the mixture was washed with 5% aqueous sodium hydrogen carbonate solution (100 mL) once, 50% aqueous DMF solution (200 mL) five times, water (100 mL) twice, and 10% aqueous sodium chloride solution (100 mL) once. Thereafter, the organic layer was concentrated, and purified by a silica gel column chromatography to obtain the desired product (22.72 g).

Preparation Example 10

A preparation example of PMM amidite C wherein the nucleobase moiety is a cytosine is shown below.

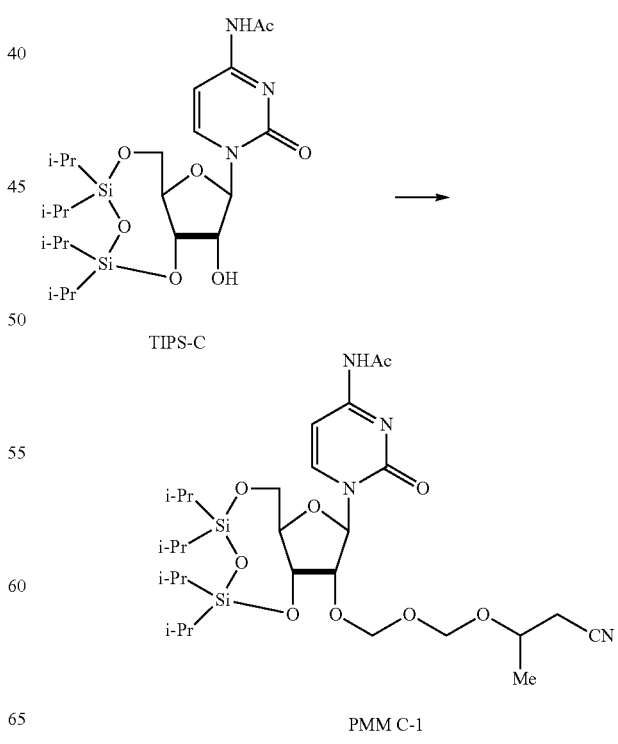

TIPS-C

PMM C-1

TIPS-C (50.0 g) and toluene (250 mL) were placed in a flask, and the solution was concentrated into 150 mL. After THF (110 mL) was added thereto, the reaction solution was cooled to −50° C., and thereto were added dropwise the PMM reagent (24.9 g), a solution of N-iodosuccinimide (28.8 g) in THF (65 mL), and trifluoromethane sulfonic acid (21.3 g) in the order. After the mixture was stirred at −50° C. for 30 minutes, the reaction solution was poured to an ice-cooled solution comprised of sodium hydrogen carbonate (15.0 g), sodium thiosulfate (42.5 g), water (275 mL), and toluene (170 mL), and the mixture was separated with a separatory funnel at room temperature. Next the organic layer was washed with a solution of sodium hydrogen carbonate (9.0 g), sodium thiosulfate (25.0 g) and water (165 mL). The organic layer was further washed with a solution of sodium chloride (25.0 g) and water (250 mL), and the organic layer was concentrated to 150 mL. A procedure of addition of THF (200 mL) thereto and concentration of the resulting mixture to 150 mL was repeated twice to obtain a crude product containing the desired PMM C-1. Exact Mass: 654.3, Actual Mass: 653.4 (ESI (−)).

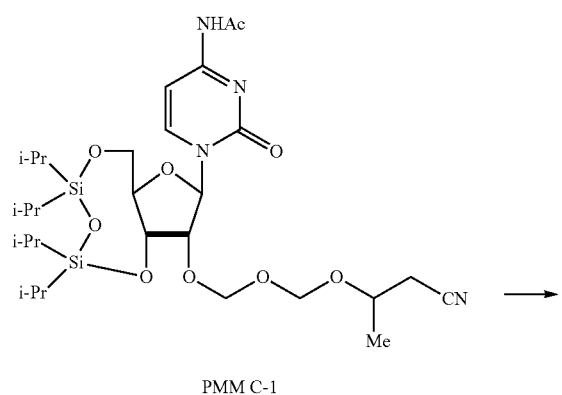

PMM C-1

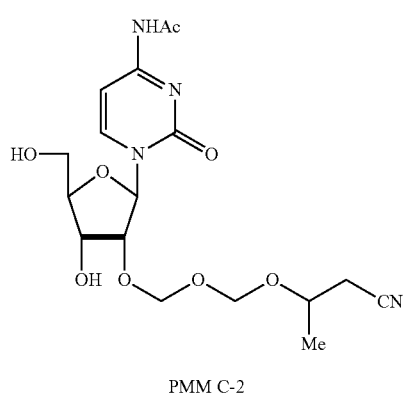

PMM C-2

To the solution of crude PMM C-1 in THF (150 mL) were added THF (50 mL) and hydrogen trifluoride/triethylamine (16.8 g) at 25° C., and the mixture was stirred for 15 hours. The reaction solution was cooled to 0° C., and thereto was added dropwise tert-butyl methyl ether (200 mL) and the mixture was stirred for 1 hour. The reaction solution was filtered, and the materials remained on the filter were washed with tert-butyl methyl ether (100 mL), and the resulting solids were dried under reduced pressure to obtain a crude product (41.8 g) containing the desired product. Exact Mass: 412.2, Actual Mass: 411.2 (ESI (−)).

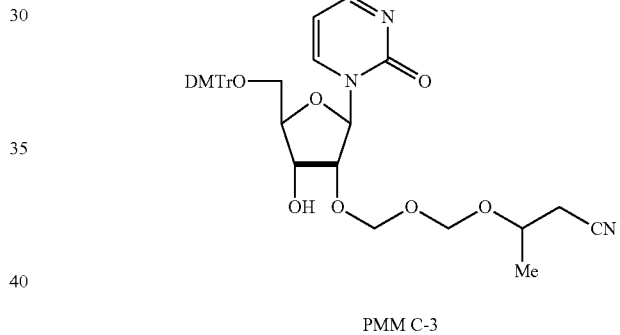

PMM C-2

PMM C-3

To the crude PMM C-2 (41.8 g) was added pyridine (200 mL), and the mixture was concentrated to 120 mL. Thereto was further added pyridine (80 mL), and the mixture was concentrated to 120 mL. Thereto were added pyridine (80 mL), toluene (200 mL), and acetonitrile (80 mL), and the reaction solution was cooled to 0° C. Thereto was added 4,4′-dimethoxytrityl chloride (38.5 g), and the mixture was stirred at 20° C. for 2.5 hours. Thereto was added methanol (20 mL) and the mixture was stirred for 5 minutes, and then the resulting mixture was added, with toluene (40 mL) rinse, to a solution of sodium hydrogen carbonate (6.0 g) in water (120 mL), and the mixture was separated with a separatory funnel at room temperature. Next, the organic layer was washed with a solution of sodium hydrogen carbonate (6.0 g) in water (120 mL) and the organic layer was concentrated to 120 mL, which was subjected to a procedure of concentration to 120 mL after addition of toluene (160 mL) three times to obtain a crude product containing the desired product. The mixture was purified by a silica gel column chromatography (silica gel 1 kg, a solution of heptane/ethyl acetate-acetone 1:1=50/50 to 20/80) to obtain the desired product (44.4 g, yield 65% from TIPS-C). Exact Mass: 714.3, Actual Mass: 713.3 (ESI (−)).

Preparation Example 11

A preparation example of PMM amidite A wherein the nucleobase moiety is an adenine is shown below.

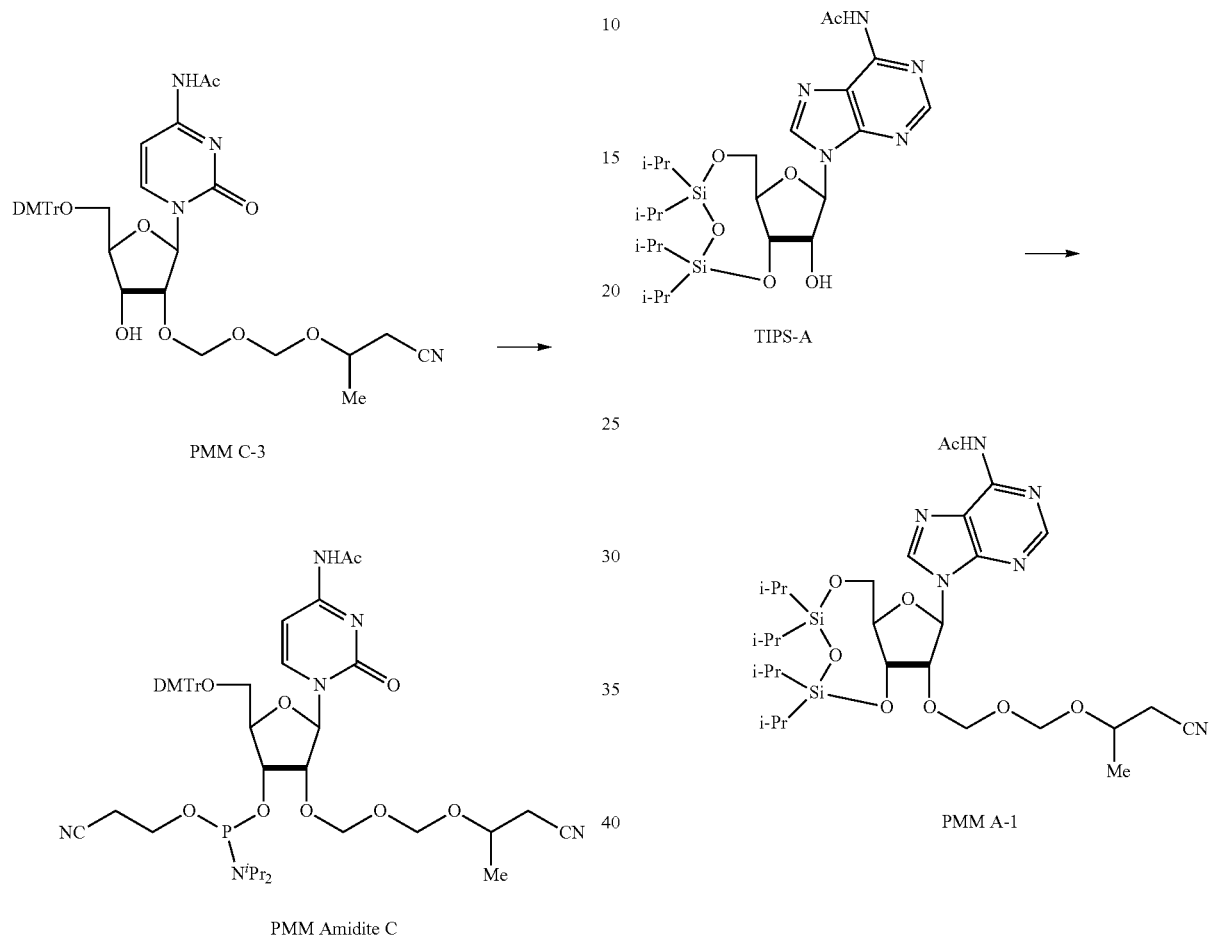

To the PMM C-3 (44.0 g) was added acetonitrile (264 mL), and the mixture was concentrated to 132 mL. Thereto were added diisopropylamine tetrazolide (12.1 g), and 2-cyanoethyl N,N,N',N'-tetraisopropyl phosphorodiamidite (22.3 g) at 25° C., and the mixture was stirred at 35° C. for 2 hours. The reaction solution was poured to a solution consisting of toluene (440 mL), water (220 mL) and sodium hydrogen carbonate (22 g), and the mixture was separated with a separatory funnel at room temperature. The organic layer was washed with a solution of DMF (220 mL) and water (220 mL) four times, water (220 mL) twice, and a solution of sodium chloride (22 g) and water (220 mL) once. To the organic layer was added sodium sulfate (22 g), and the mixture was filtered, and concentrated to 132 mL to obtain the crude product containing the desired product. The product was purified by a silica gel column chromatography (silica gel 440 g, heptane/acetone=70/30 to 40/60) to obtain the desired product (44.2 g, yield 79% from the PMM C-3).

TIPS-A (60.0 g) and toluene (350 mL) were added to a flask, and the solution was concentrated to 180 mL. After THF (120 mL) was added, the reaction solution was cooled to −10° C., and thereto were added iodine (165.54 g) and the PMM reagent (28.6 g). After the mixture was stirred at 0° C. for 2 hours, the reaction solution was poured to an ice-cooled solution of sodium hydrogen carbonate (33.6 g), sodium thiosulfate (336 g), water (480 mL) and toluene (180 mL), and the mixture was separated with a separatory funnel at room temperature. Next, the organic layer was washed with a solution of sodium hydrogen carbonate (16.8 g), sodium thiosulfate (168 g) and water (240 mL). The organic layer was further washed with a solution of sodium chloride (30.0 g) and water (300 mL), and the organic layer was concentrated to 180 mL to obtain a crude product containing the desired product. The product was purified by a silica gel column chromatography to obtain the desired product PMM A-1 (51.62 g). Exact Mass: 678.3, Actual Mass: 677.4 (ESI (−)).

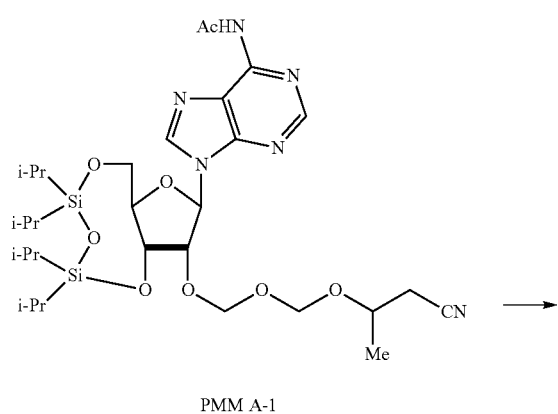

PMM A-1

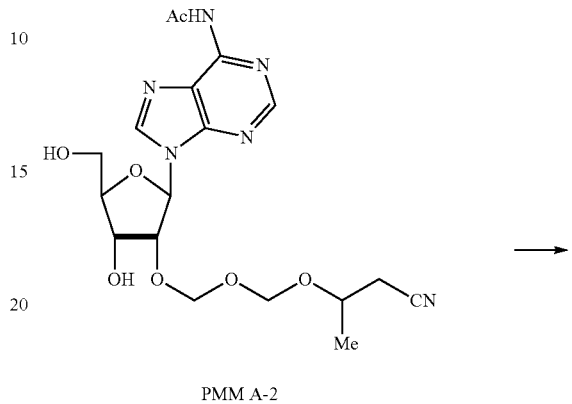

PMM A-2

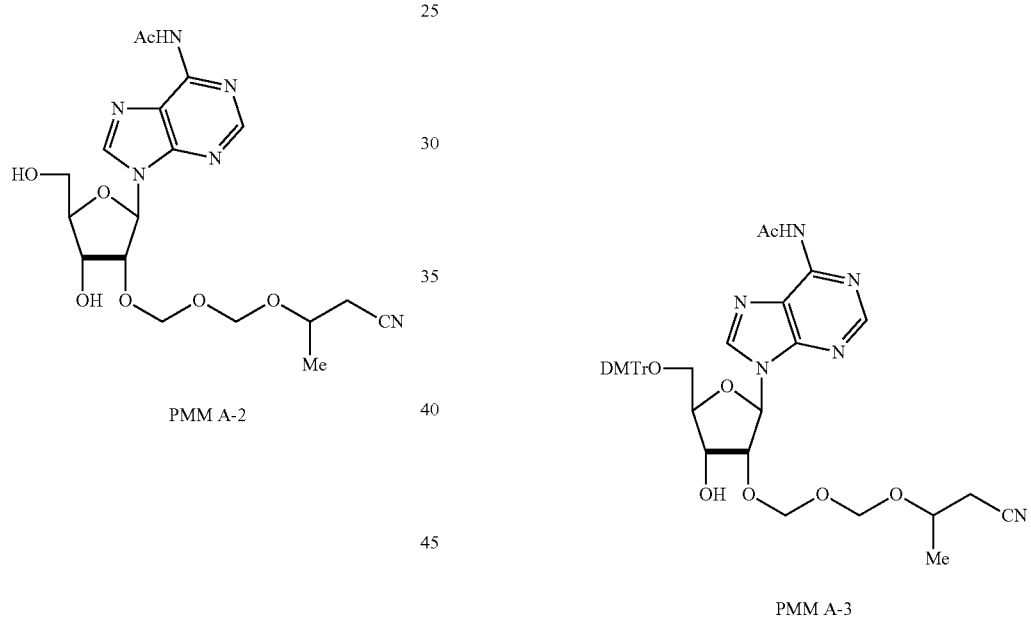

PMM A-2

PMM A-3 solubilized, the mixture was concentrated to 150 mL. Thereto was added acetonitrile (150 mL) and the mixture was concentrated to 150 mL. Thereto was added acetonitrile (150 mL) and the mixture was concentrated to 150 mL to obtain a crude product containing the desired compound PMM A-2. Exact Mass: 436.2, Actual Mass: 435.2 (ESI (−)).

To a solution of the PMM A-1 (50.0 g) in THF (200 mL) was added hydrogen trifluoride/triethylamine (13.06 g) at 20° C., and the mixture was stirred at 20 to 24° C. for 4 hours. The reaction solution was cooled to 0° C., and thereto was added heptane (500 mL), and after the mixture was stirred for 20 minutes, 330 mL of the supernatant was removed. Thereto was added heptane (300 mL), and after the mixture was stirred for 20 minutes, 300 mL of the supernatant was removed. Thereto was added heptane (300 mL) and after the mixture was stirred for 20 minutes, 300 mL of the supernatant was removed. Thereto was added tert-butyl methyl ether (200 mL) and after the mixture was stirred for 20 minutes, 200 mL of the supernatant was removed. After the mixture was raised to room temperature, thereto was added acetonitrile (300 mL), and after the precipitates were To a total amount of the crude PMM A-2 were added pyridine (100 mL) and toluene (350 mL) and the reaction solution was cooled to 0° C. Thereto was added 4,4'-dimethoxytritylchloride (29.95 g) and the mixture was stirred at 20 to 23° C. for 5 hours. Thereto was added methanol (16 mL) and after the mixture was stirred for 5 minutes, the mixture was transferred, with toluene (64 mL) rinse, to a 5% aqueous sodium hydrogen carbonate solution, and separated with a separatory funnel at room temperature.

Next the obtained organic layer was washed with a 5% aqueous sodium hydrogen carbonate solution (100 mL), and was further washed with a 10% aqueous sodium chloride solution (100 mL), and the organic layer was concentrated to 96 mL. The mixture was subjected to a procedure of concentration to 96 mL after addition of toluene (128 mL) three times to obtain a crude product containing the desired product. The product was purified by a silica gel column chromatography to obtain the desired product PMM A-3 (40.56 g). Exact Mass: 738.3, Actual Mass: 737.4 (ESI (−)).

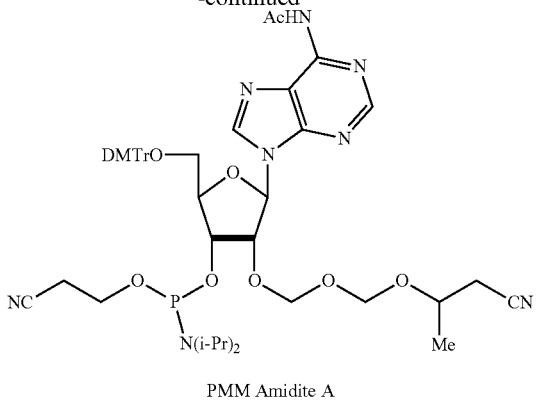

PMM Amidite A

To the PMM A-3 (40.0 g) were added acetonitrile (120 mL), diisopropylamine tetrazolide (10.8 g) and 2-cyanoethyl N,N,N',N'-tetraisopropyl phosphorodiamidite (19.6 g) at 25° C., and the mixture was stirred at 36 to 38° C. for 3 hours. The reaction solution was poured to a solution consisting of toluene (400 mL) and a 5% aqueous sodium carbonate solution (200 mL), and the mixture was separated with a separatory funnel at room temperature. The organic layer was washed with a 50% aqueous DMF solution (400 mL) four times, water (220 mL) twice, and an aqueous sodium chloride solution (200 mL) once. To the organic layer was added sodium sulfate (20 g), and the mixture was filtered, and concentrated to 120 mL to obtain a crude product containing the desired product. The mixture was purified by a silica gel column chromatography to obtain the desired product PMM A amidite (46.35 g).

Preparation Example

The spectra data of the amidite of the Preparation Examples 9 to 11 are shown below.

TABLE 1

White solid
$^{31}$P-NMR (CDCl$_3$): δ 151.93, 150.82 (ppm)

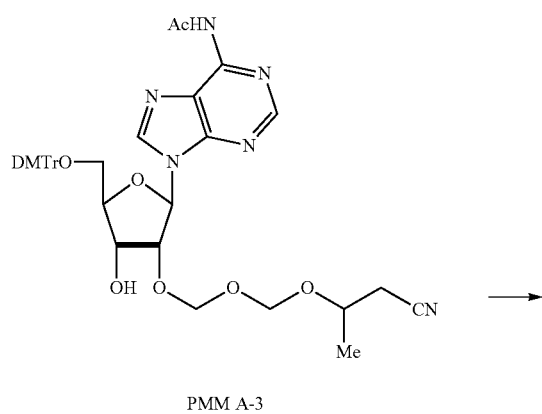

PMM A-3

Preparation Example 9
PMM amidite U

TABLE 1-continued

| Preparation Example 10 PMM amidite C | White solid <br> $^{31}$P-NMR (CDCl$_3$): δ 152.22, 150.69 (ppm) |
|---|---|
| Preparation Example 11 PMM amidite A | White solid <br> $^{31}$P-NMR (CDCl$_3$): δ 151.59, 151.44 (ppm) |

Preparation Examples 12 to 16

In a similar manner as in the Examples above, the PMM amidite G, the BMM amidite U, the TBM amidite U, as well as a reference compound, PMM 2 amidite U and the CPM amidite C were prepared.

The spectra data of the prepared amidites were shown below.

TABLE 2

| | White solid <br> $^{31}$P-NMR (CDCl$_3$): δ 151.77, 151.67, 151.33, 151.26 (ppm) |
|---|---|

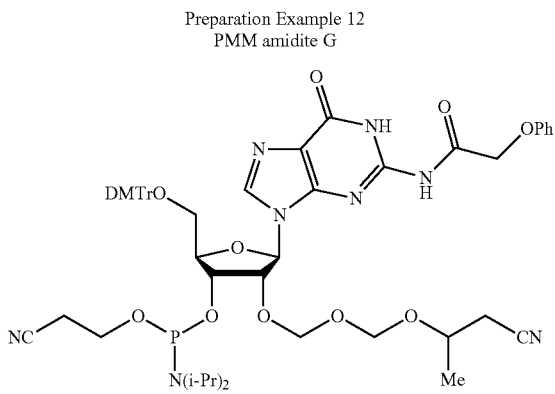

Preparation Example 12
PMM amidite G

TABLE 2-continued
Preparation Example 13
BMM amidite U
White solid
$^{31}$P-NMR (CDCl$_3$): δ 152.07, 152.01, 150.93, 150.84 (ppm)
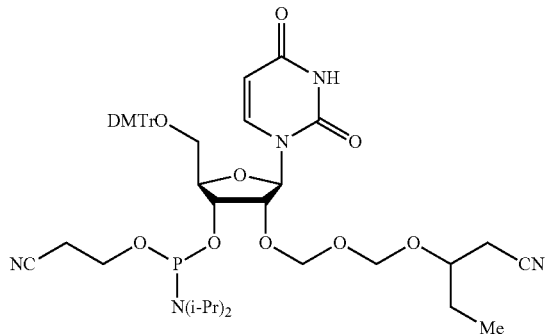
Preparation Example 14
TBM amidite U
White solid
$^{31}$P-NMR (CDCl$_3$): δ 151.94, 150.89 (ppm)
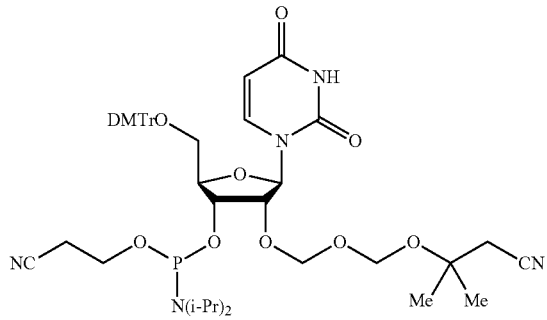
TABLE 3
Preparation Example 15
PMM2 amidite U
White solid
$^{31}$P-NMR (CDCl$_3$): δ 151.97, 150.69 (ppm)
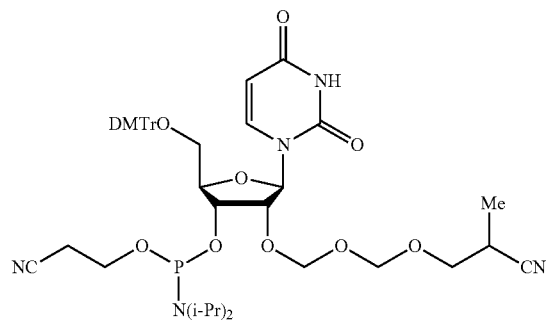

TABLE 3-continued

| Preparation Example 16 CPM amidite C | White solid $^{31}$P-NMR (CDCl$_3$): δ 152.64, 152.14, 150.66, 150.46 (ppm) |

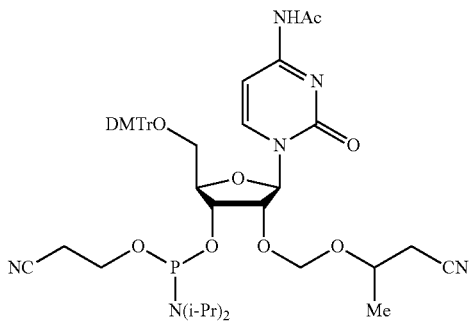

Preparation Example 1 of Nucleic Acid

Using the PMM amidite U, the BMM amidite U and the TBM amidite U, which were prepared in the preparation examples above, uridine 50 mer indicated below as Sequence No. 1 was synthesized.

5'-UUUUUUUUUU UUUUUUUUUU UUUUUUUUUU UUUUUUUUUU UUUUUUUUUU-3' (Sequence No. 1) (wherein u represents uridine monohydrate sodium salt).

An oligonucleotide acid was synthesized from 3' side toward 5' side thereof using Nts M-4MX-E (manufactured by NIHON TECNO SERVICE CO., LTD) as a nucleic acid synthesizer. For the synthesis, a porous glass was used as a solid support, a trichloroacetic acid with high purity was used as a deblocking solution, 5-benzylmecapto-1H-tetrazole was used as a condensing agent, iodine solution was used as an oxidizing agent, and a phenoxy acetic acid solution and N-methyl imidazole solution were used as a capping solution.

The measurement of the purity of oligonucleotide crude product after solid phase synthesis was conducted by HPLC. The crude product was separated to each ingredient by HPLC (wavelength 260 nm, column: ACQITY UPLC Oligonucleotide BHE, C18, 2.1×100 mm), and the purity of the oligonucleotide was calculated from an area value of a main product relative to total area value of the resulting chromatogram.

Example 1

As a result of the synthesis of uridine 50 mer (molecular weight 15246.53) using the PMM amidite U, the purity of OD$_{260}$ per 0.406 μmol was 97.48 OD, and the purity of the product was 84.3%. From the OD$_{260}$ value, the yield per 1 μmol was calculated as 9604 μg/μmol. The results are shown in Table 4.
(Note: OD$_{260}$ represents an absorbance of UV$_{260}$ nm per 10 mm optical path length for 1 mL solution (pH=7.5). Since it is in general known to be 1OD=40 μg for RNA, the yield of RNA can be calculated from the absorbance).

Example 2

As a result of a synthesis of uridine 50 mer (molecular weight 15246.53) using the BMM amidite U, the purity of OD$_{260}$ per 0.200 μmol was 48.51 OD, and the purity of the product was 72.5%. From the OD$_{260}$ value, the yield per 1 μmol was calculated as 9702 μg/μmol. The results are shown in Table 4.

Example 3

As a result of a synthesis of uridine 50 mer (molecular weight 15246.53) using the TBM amidite U, the purity of OD$_{260}$ per 1.074 μmol was 249.74 OD, and the purity of the product was 66.2%. From the OD$_{260}$ value, the yield per 1 μmol was calculated as 9301 μg/μmol. The results are shown in Table 4.

Comparative Example 1

Whilst, a similar solid phase synthesis was conducted by using the PMM 2 amidite U which was obtained in the Reference Preparation to prepare uridine 50 mer, and as the result, the purity of OD$_{260}$ per 0.406 μmol was 100.81 OD, and the purity of the product was 50.4%. From the OD$_{260}$ value, the yield per 1 μmol was calculated as 9932 μg/μmol. The results are shown in Table 4.

Comparative Example 2

Uridine 50 mer (molecular weight 15246.53) was synthesized by using the uridine EMM amidite which is described in Example 2 of Japanese Patent No. 5554881 B2, and as the result, the purity of OD$_{260}$ per 1.028 μmol was 245.91 OD, and the purity of the product was 55.8%. From the OD$_{260}$ value, the yield per 1 μmol was calculated as 9568 μg/μmol. The results are shown in Table 4.

TABLE 4

| | Example 1 | Example 2 | Example 3 | Comparative Example 1 | Comparative Example 2 |
|---|---|---|---|---|---|
| Uridine 50 mer Purity (%) | 84.3 | 72.5 | 66.2 | 50.4 | 55.8 |
| Yield (μg/μmol) | 9604 | 9702 | 9301 | 9932 | 9568 |

As shown in the above Table 4, the good results of the purity of the uridine 50 mer was obtained.

Example 4

The preparation method of a synthetic intermediate PMM A-1 wherein the nucleobase moiety is adenine is shown below.

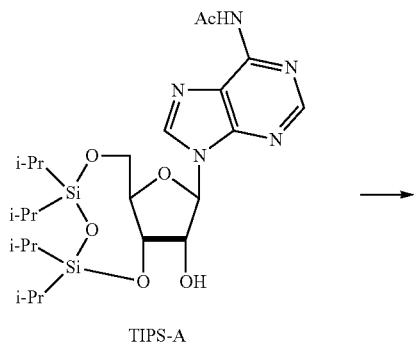

TIPS-A

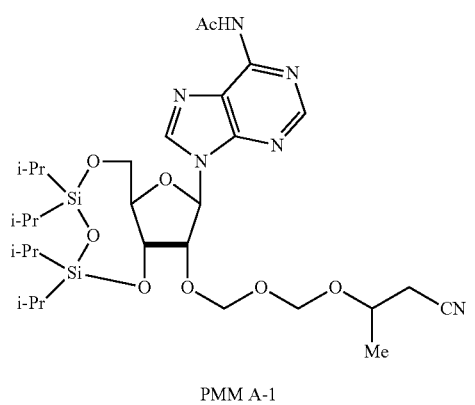

PMM A-1

TIPS-A (5.00 g) and toluene (25 mL) were placed in a flask, and the solution was concentrated to 15 mL. Toluene (10 mL) was added to the flask, and the solution was concentrated to 15 mL. After 4-methyltetrahydropyran (10 mL) was added as a solvent, the reaction solution was cooled to −10° C., and thereto were added iodine (13.8 g) and the PMM-conversion reagent (2.38 g). After the mixture was stirred at 0° C. for 1 hour, the reaction solution was poured into an ice-cooled solution consisting of sodium hydrogen carbonate (2.8 g), sodium thiosulfate (28 g), water (40 mL) and toluene (25 mL), and the mixture was separated with a separatory funnel at room temperature. The organic layer was analyzed by LC, and the area percentage of the desired PMM A-1 was calculated. Exact Mass: 678.3, Actual Mass: 677.4 (ESU (−)). The results are shown in Table 5.

Example 5

The reaction was conducted in a similar manner as in Example 4 except for using the same amounts of tetrahydrofuran (THF) in place of 4-methyltetrahydropyran as a solvent to prepare the PMM A-1. The results are shown in Table 5.

Example 6

The reaction was conducted in a similar manner as in Example 4 except for using dioxane in place of 4-methyltetrahydropyran as a solvent and changing the stirring time to 3.5 hours, to prepare the PMM A-1. The results are shown in Table 5.

TABLE 5

|  | Example 4 | Example 5 | Example 6 |
|---|---|---|---|
| Solvent | 4-Methyl tetrahydropyran | THF | Dioxane |
| Stirring time | 1 h | 1 h | 3.5 h |
| PMM A-1 Area percentage | 96.8% | 92.6% | 50.2% |

As shown in the above Table 5, the good results of the production yield of synthetic intermediate were obtained.

Preparation Example 2 of Nucleic Acid

Sequence (A): 5'-AGCAGAGUACACACAG-CAUAUACC-P-GGUAUAUGCUGUGUGUACUCUGC-UUC-P-G-3' (Sequence Nos. 2 and 3) 53 mer In the sequence (A), P represents a partial structure which is separated with a wavy line in the following chemical formula.

AGCAGAGUAC ACACAGCAUA UACC (Sequence No. 2)
GGUAUAUGCU GUGUGUACUC UGCUUC (Sequence No. 3)

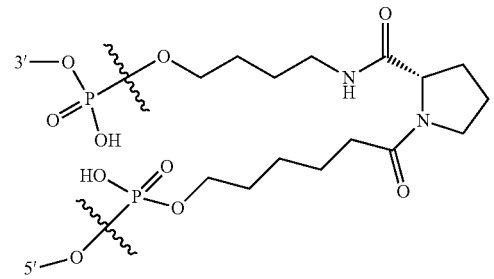

The oligonucleotide consisting of the sequence (A) was synthesized by using AKTA Oligopilot 100 plus (manufactured by GE Healthcare) as a nucleic acid synthesizer according to a phosphoramidite solid phase synthesis method to synthesize the oligonucleotide consisting of the sequence (A) from 3' side toward 5' side thereof. For the synthesis, a porous glass was used as a solid support, a trichloroacetic acid with high purity was used as a deblocking solution, 5-benzylmecapto-1H-tetrazole was used as a condensing agent, iodine solution was used as an oxidizing agent, and a phenoxy acetic acid solution and N-methyl imidazole solution were used as a capping solution.

[Measurement of Yields of Oligonucleotide]

The $OD_{260}$ of the crude product was measured. $OD_{260}$ represents an absorbance of $UV_{260}$ run per 10 mm optical path length for 1 mL solution (pH=7.5). Since it is in general known to be 1OD 40 μg for RNA, the yield of RNA can be calculated on the basis of the measurement value of $OD_{260}$. With respect to the Example 7 and the Comparative Example 3, a relative yield of product per 1 μmol of product of the Example 7 was calculated, and the results are shown in Table 6.

Example 7

The oligonucleotides consisting of the sequence (A) were synthesized by using the PMM amidite U, the PMM amidite C, the PMM amidite A, the PMM amidite G and the compound (3) described in WO 2017/188042, and as the result, the purity thereof was 60.8%. The results of the purity and the relative yield per 1 μmmol are shown in Table 6.

Comparative Example 3

The oligonucleotides consisting of the EMM amidite U described in Example 2 of US 2012/0035246, the EMM amidite C described in Example 3 of the same, the EMM amidite A described in Example 4 of the same, the EMM amidite G descried in Example 5 of the same as well as the compound (3) described in WO 2017/188042 were synthesized, and as the result, the purity was 53.0%. The results of the purity and the relative yield per 1 μmmol are shown in Table 6.

TABLE 6

|  | Example 7 | Comparative Example 3 |
|---|---|---|
| Oligonucleotide of Sequence (A) Purity (%) | 60.8 | 53.0 |
| Relative yield per 1 μmmol | 1.00 | 1.01 |

As shown in the above Table 6, the good results of the purity of the oligonucleotide of Sequence (A) can be obtained.

[Free Text of Sequence Listing]

Sequence No. 1 in the Sequence List represents a nucleotide sequence of uridine 50 mer.

Sequence Nos. 2 and 3 in the Sequence List represent a nucleotide sequence of oligonucleotide composed of the sequence that is prepared in Preparation Example 2 of nucleic acid.

The invention claimed is:

1. An amidite compound represented by formula (1):

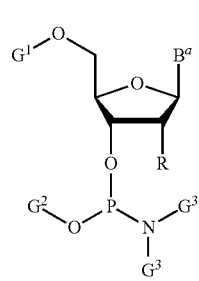
(1)

wherein
R represents a formula:

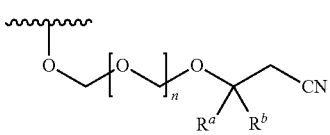

wherein
R$^a$ and R$^b$ are identical to or different from each other and each represents a methyl group, an ethyl group, or a hydrogen atom, with the proviso that R$^a$ and R$^b$ do not represent a hydrogen atom at the same time,
n represents an integer of 1 to 5,
B$^a$ represents a group containing optionally-protected nucleobase structure,
G$^1$ and G$^2$ are identical to or different from each other and each represents a protecting group for a hydroxy group, and
G$^3$ are identical to or different from each other and each represents an alkyl group.

2. The amidite compound according to claim 1 wherein R$^a$ represents a methyl group or an ethyl group, and R$^b$ represents a hydrogen atom.

3. The amidite compound according to claim 1 wherein G$^1$ represents the following group:

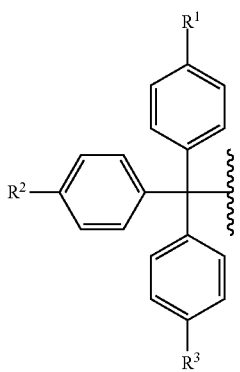

wherein
R$^1$, R$^2$ and R$^3$ are identical to or different from each other, and each represents a hydrogen atom or an alkoxy group.

4. The amidite compound according to claim 1 wherein G$^2$ represents the group:

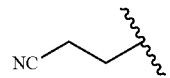

5. The amidite compound according to claim 1 wherein G$^3$ represents an isopropyl group.

6. A method for preparing a compound containing a polynucleotide structure represented by formula (2):

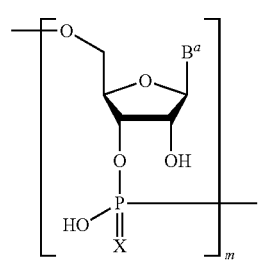
(2)

wherein
B$^a$ is identical to or different from each other and each represents a group containing optionally-protected nucleobase structure,
X represents an oxygen atom or a sulfur atom, and
m is a positive integer,
which comprises a step of subjecting the amidite compound according to claim 1 to a solid phase synthesis reaction.

7. The method according to claim 6 wherein the compound containing the polynucleotide structure represented by formula (2) is a compound resulting from the step of reacting a compound represented by formula (3):

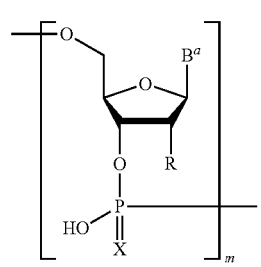
(3)

wherein
B$^a$ is identical to or different from each other and each represents a group containing optionally-protected nucleobase structure,
X represents an oxygen atom or a sulfur atom,
R is identical to or different from each other and each represents a formula:

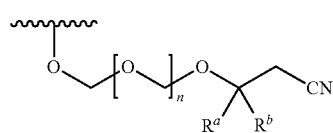

wherein
  $R^a$ and $R^b$ are identical to or different from each other and each represents a methyl group, an ethyl group, or a hydrogen atom, with the proviso that $R^a$ and $R^b$ do not represent a hydrogen atom at the same time,
  n represents an integer of 1 to 5,
  m is a positive integer,
which is resulting from a solid phase synthesis reaction utilizing the amidite compound, with tetraalkylammonium fluoride.

8. The method according to claim 7 wherein $R^a$ represents a methyl group or an ethyl group, and $R^b$ represents a hydrogen atom.

9. The method according to claim 7 wherein n=1.

10. An ether compound represented by formula (4):

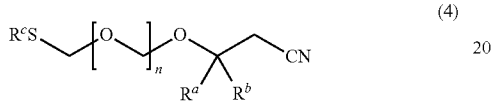
(4)

wherein $R^a$, $R^b$ and n are the same as defined in claim 1, and $R^c$ represents a C1-C6 alkyl group or a phenyl group.

11. The ether compound according to claim 10 wherein $R^a$ represents a methyl group or an ethyl group, $R^b$ represents a hydrogen atom, and $R^c$ represents a methyl group.

12. The compound according to claim 10 wherein n=1.

13. A method for preparing an ether compound represented by formula (7):

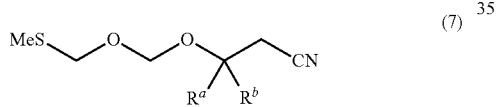
(7)

wherein
  $R^a$ and $R^b$ are the same as defined below,
which comprises the steps of:
(a): reacting a compound represented by formula (5):

(5)

wherein $R^a$ and $R^b$ are identical to or different from each other and each represents a methyl group, an ethyl group, or a hydrogen atom, with the proviso that $R^a$ and $R^b$ do not represent a hydrogen atom at the same time, with a cyanide ion, and (b): reacting 3-hydroxyalkylnitrile represented by formula (6):

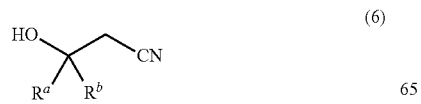
(6)

wherein
  $R^a$ and $R^b$ are the same as defined above,
resulting from step (a), with bis(methylthiomethyl)ether in a solvent in the presence of an oxidizing agent and an acid.

14. The method according to claim 13 wherein $R^a$ represents a methyl group or an ethyl group, and $R^b$ represents a hydrogen atom.

15. The method according to claim 13 wherein $R^a$ represents a methyl group, and $R^b$ represents a hydrogen atom.

16. The method according to claim 15 for preparing a compound represented by formula (8):

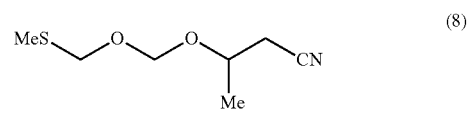 [SMILES: CSCOCOC(C)CC#N]
(8)

which comprises the steps of:
A: hydrolyzing 3-aminocrotononitrile,
B: reducing the cyanoacetone obtained by the step A to obtain 3-hydroxybutanenitrile, and
C: reacting the 3-hydroxybutanenitrile obtained by the step B with bis(methylthiomethyl)ether in a solvent in the presence of an oxidizing agent and an acid.

17. A method for preparing a compound represented by formula (10):

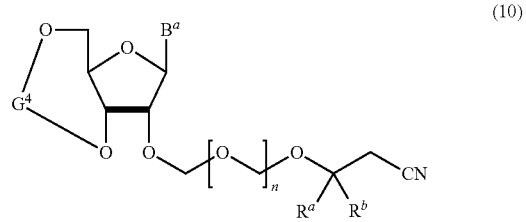
(10)

wherein
  $B^a$, $R^a$, $R^b$, n and $G^4$ are the same as defined below,
which comprises reacting a compound represented by formula (9):

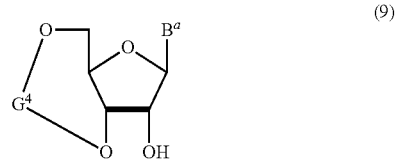
(9)

wherein
  $B^a$ represented a compound containing optionally-protected nucleobase structure, and $G^4$ represents a protecting group for a hydroxy group,
with a compound represented by formula (4):

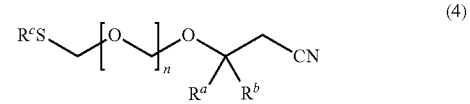
(4)

wherein
R$^a$ and R$^b$ are identical to or different from each other and each represents a methyl group, an ethyl group, or a hydrogen atom, with the proviso that R$^a$ and R$^b$ do not represent a hydrogen atom at the same time,
R$^c$ represents a C1-C6 alkyl group or a phenyl group, and
n is an integer of 1 to 4,
in the presence of an oxidizing agent.

18. The method according to claim 17 wherein tetrahydropyran or 4-methyltetrahydropyran is used as a reaction solvent.

19. The method according to claim 17 wherein G$^4$ represents a group represented by a G$^4$-1 or G$^4$-2 structure.

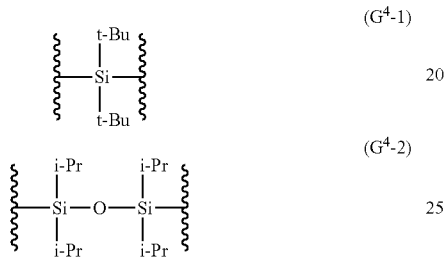

20. A method for preparing the compound represented by formula (1) as defined in claim 1, which comprises further steps of:
deprotecting the compound represented by formula (10) to obtain the compound represented by formula (11):

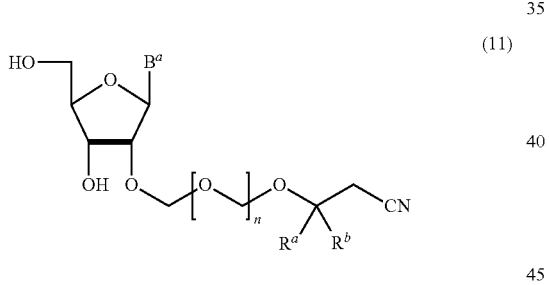

wherein
B$^a$, R$^a$, R$^b$ and n are the same as defined above,
protecting selectively the hydroxy group at 5' position of the compound represented by formula (11) to obtain a compound represented by formula (12):

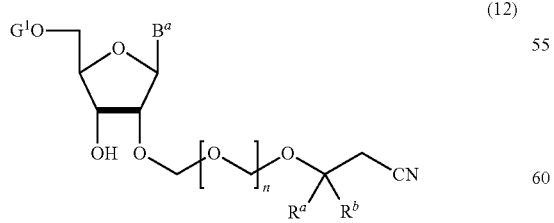

wherein
B$^a$, R$^a$, R$^b$ and n are the same as defined above, and G$^1$ represents a protecting group for a hydroxy group, and reacting the compound represented by formula (12) with a phosphorodiamidite represented by formula (13):

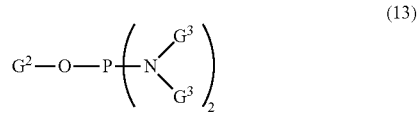

wherein
G$^2$ represents a protecting group for a hydroxy group, and G$^3$ are identical to or different from each other and each represents an alkyl group.

21. A compound represented by formula (10):

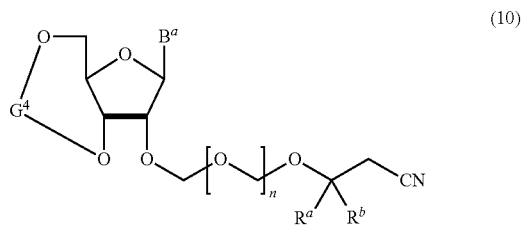

wherein
R$^a$ and R$^b$ are identical to or different from each other, and each represents a methyl group, an ethyl group, or a hydrogen atom, with the proviso that R$^a$ and R$^b$ do not represent a hydrogen atom at the same time,
n is an integer of 1 to 5,
B$^a$ represents a group containing an optionally protected nucleobase structure, and
G$^4$ represents a protecting group.

22. A compound represented by formula (11):

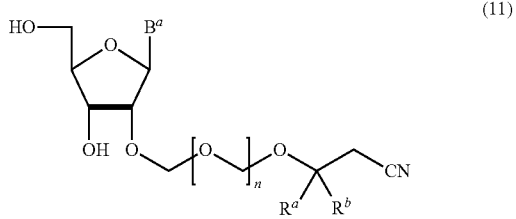

wherein
B$^a$, R$^a$, R$^b$ and n are the same as defined in claim 21.

23. A compound represented by formula (12):

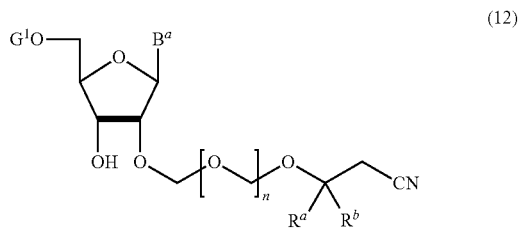

wherein
B$^a$, R$^a$, R$^b$ and n are the same as defined in claim 21, and G$^1$ represents a protecting group of a hydroxy group.

\* \* \* \* \*